(12) United States Patent
Jackson

(10) Patent No.: US 9,448,183 B2
(45) Date of Patent: *Sep. 20, 2016

(54) AVIONIC DISPLAY TESTING SYSTEM

(71) Applicant: The Boeing Company, Chicago, IL (US)

(72) Inventor: Timothy Edward Jackson, Mukilteo, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/275,278

(22) Filed: May 12, 2014

(65) Prior Publication Data
US 2014/0247341 A1    Sep. 4, 2014

Related U.S. Application Data

(63) Continuation of application No. 13/019,416, filed on Feb. 2, 2011, now Pat. No. 8,736,679.

(51) Int. Cl.
H04N 7/18      (2006.01)
G09B 9/32      (2006.01)
G01N 21/88     (2006.01)
B64F 5/00      (2006.01)
G01C 23/00     (2006.01)
G01C 25/00     (2006.01)
G09G 3/00      (2006.01)

(52) U.S. Cl.
CPC ............ *G01N 21/88* (2013.01); *B64F 5/0045* (2013.01); *G01C 23/00* (2013.01); *G01C 25/00* (2013.01); *G09G 3/006* (2013.01); *G09G 2380/12* (2013.01)

(58) Field of Classification Search
None
See application file for complete search history.

(56) References Cited

U.S. PATENT DOCUMENTS

| 4,513,318 | A | 4/1985 | Wilensky et al. |
| 5,036,479 | A | 7/1991 | Prednis et al. |
| 5,303,152 | A | 4/1994 | Moses et al. |
| 5,606,734 | A * | 2/1997 | Bahu ............................ 455/303 |
| 6,791,476 | B1 | 9/2004 | Hedrick |
| 2007/0236366 | A1 | 10/2007 | Gur et al. |
| 2010/0214411 | A1* | 8/2010 | Weinmann et al. .......... 348/148 |
| 2012/0194666 | A1 | 8/2012 | Jackson |

FOREIGN PATENT DOCUMENTS

CN    101354485 A    1/2009
WO    WO2010129760 A2    11/2010

OTHER PUBLICATIONS

Office Action, dated Jun. 3, 2013, regarding U.S. Appl. No. 13/019,416, 16 pages.
Final Office Action, dated Oct. 17, 2013, regarding U.S. Appl. No. 13/019,416, 20 pages.
Notice of Allowance, dated Jan. 17, 2014, regarding U.S. Appl. No. 13/019,416, 13 pages.

(Continued)

*Primary Examiner* — Behrooz Senfi
*Assistant Examiner* — Maryam Nasri
(74) *Attorney, Agent, or Firm* — Yee & Associates, P.C.

(57) ABSTRACT

A method and apparatus for testing a number of display devices. Images displayed on the number of display devices are received by a computer system for a platform during a performance of a number of tests at a number of test locations for the platform. A portion of the images from the images are identified as a number of images of interest using a policy.

21 Claims, 12 Drawing Sheets

(56) References Cited

OTHER PUBLICATIONS

European Search Report, dated Apr. 23, 2014, regarding Application No. EP12153712.0, 7 pages.
English Translation of Text of the First Office Action, dated Dec. 31, 2014, regarding Application No. 201210022374.4, 22 pages.
English Translation of Text of the Second Office Action, issued Jul. 29, 2015, regarding Application No. 201210022374.4, 23 pages.
State Intellectual Property Office of China Third Notification of Office Action and English translation, issued Dec. 21, 2015, 18 pages.
Notice of Reasons for Rejection and English Translation, regarding Japanese Patent Application No. 2012-010076, Issued Dec. 1, 2015, 5 pages.

* cited by examiner

AVIONIC DISPLAY TESTING SYSTEM

This application is a continuation application of U.S. patent application Ser. No. 13/019,416, filed Feb. 2, 2011.

BACKGROUND INFORMATION

1. Field

The present disclosure relates generally to aircraft and, in particular, to display devices in aircraft. Still more particularly, the present disclosure relates to a method and apparatus for testing display devices in an aircraft.

2. Background

In aircraft, information used by pilots to operate the aircraft is received from flight instruments in the cockpit of the aircraft. These flight instruments provide information, such as, for example, height, speed, altitude, and/or other suitable information about the aircraft. These flight instruments are particularly useful when poor visibility is present.

Flight instruments may include, for example, an altimeter, an attitude indicator, an airspeed indicator, a magnetic compass, a heading indicator, a turn indicator, a vertical speed indicator, and/or other suitable types of indicators. Traditionally, these types of instruments are analog and physical instruments connected to the various sensors to provide the information to the pilot.

Increasingly, these flight instruments are represented using graphical user interfaces displayed on a display system in which the graphical user interfaces are generated by a computer system. The computer system generates video data to display the information to the operators of aircraft. These graphical user interfaces may simulate a representation of physical gauges.

For example, an airspeed indicator in the form of a circular instrument having a pointer that rotates about an axis to point to airspeed markings on the instrument may be represented in a graphical form. The same circular instrument may be displayed on a graphical user interface with a pointer that rotates to point to airspeed markings displayed on a graphical user interface to indicate the airspeed. In this manner, the graphical user interface provides familiar indications of airspeed to an operator of the aircraft. In other cases, this information may be represented in other ways, such as with a number displayed on the display device, a bar graph, and/or some other suitable type of graphical indicator.

These types of display systems provide flexibility in presenting information to an operator of an aircraft. For example, with these types of displays, different instruments may be displayed, depending on the phase of flight or based on selections by the operator. Also, the same display devices may be used in different types of aircraft with different user interfaces being generated for the specific type of aircraft on which the display devices are used. Additionally, the use of a computer system to process sensor information may provide a more accurate display of information to the operator.

With these types of display systems, however, situations may occur in which an operator of an aircraft may lose confidence in the accuracy of the information being displayed. For example, if a parameter being displayed becomes distorted temporarily, is missing intermittently, or if the display device blinks on and off, the operator may lose confidence in the accuracy of the information being displayed on the display system.

Therefore, it would be advantageous to have a method and apparatus that takes into account at least some of the issues discussed above, as well as possibly other issues.

SUMMARY

In one advantageous embodiment, a method is provided for testing a number of display devices. Images displayed on the number of display devices are received by a computer system for a platform during a performance of a number of tests at a number of test locations for the platform. A portion of the images from the images are identified as a number of images of interest using a policy.

In another advantageous embodiment, a method is provided for testing a display device for an aircraft. Information generated by a computer system for the aircraft is displayed on the display device. First images from a number of cameras directed at the display device are received. The first images comprise first timestamps for the first images. A parameter in the aircraft is changed at a selected time. In response to a change in the parameter in the aircraft, second images are received from the number of cameras. The second images comprise second timestamps for the second images. The second images are compared with corresponding first images to form a comparison. A number of images of interest are identified from the comparison using a policy.

In yet another advantageous embodiment, an apparatus comprises an image acquisition system and a computer system. The image acquisition system is configured to obtain images generated for display on a number of display devices for a platform during a performance of a number of tests at a number of test locations for the platform. The computer system is configured to receive the images from the image acquisition system and identify a portion of the images as a number of images of interest using a policy.

In still yet another advantageous embodiment, an aircraft display system comprises a display system associated with an aircraft, an image acquisition system associated with the aircraft, and a testing module associated with the aircraft. The display system comprises a number of display devices. The image acquisition system is configured to obtain images generated for display on the display system associated with the aircraft during operation of the aircraft. The testing module is configured to receive the images from the image acquisition system, identify a portion of the images as a number of images of interest using a policy, and display the number of images of interest on a display device.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof, will best be understood by reference to the following detailed description of an advantageous embodiment of the present disclosure when read in conjunction with the accompanying drawings, wherein:

DETAILED DESCRIPTION

Figure 1:
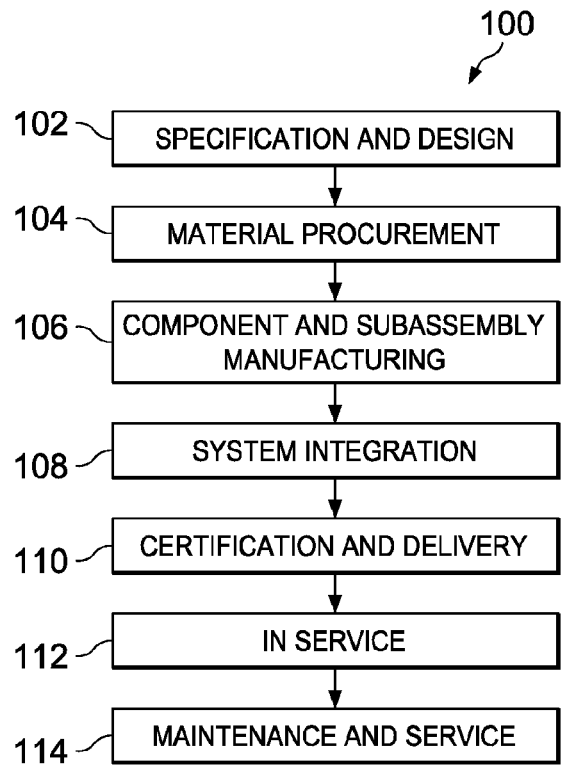
FIG. 1 is an illustration of an aircraft manufacturing and service method in accordance with an advantageous embodiment.
Figure 2:
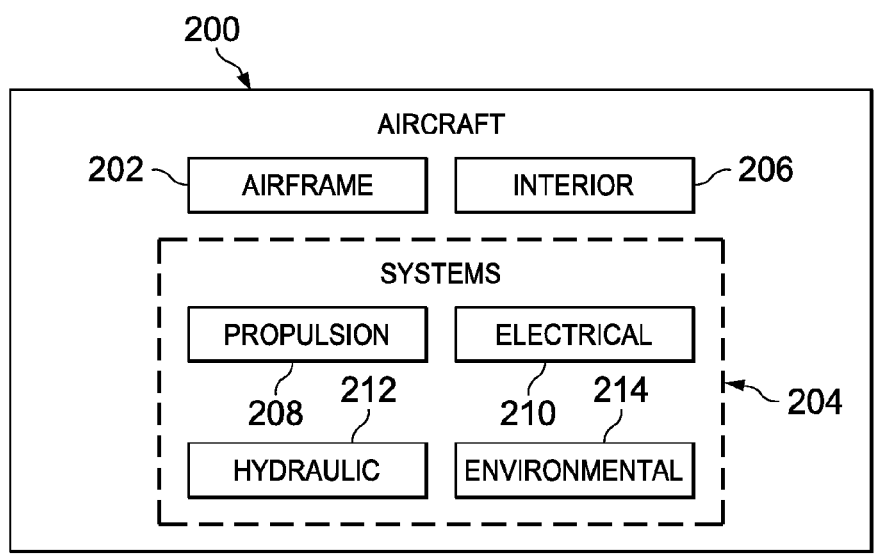
FIG. 2 is an illustration of an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service 112 by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during at least one of the stages of aircraft manufacturing and service method 100 in FIG. 1. As used herein, the phrase "at least one of", when used with a list of items, means that different combinations of one or more of the listed items may be used and only one of each item in the list may be needed. For example, "at least one of item A, item B, and item C" may include, for example, without limitation, item A, or item A and item B. This example also may include item A, item B, and item C, or item B and item C.

In one illustrative example, components or subassemblies produced in component and subassembly manufacturing 106 in FIG. 1 may be fabricated or manufactured in a manner similar to components or subassemblies produced while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A number, when referring to items, means one or more items. For example, a number of apparatus embodiments is one or more apparatus embodiments. A number of apparatus embodiments, method embodiments, or a combination thereof may be utilized while aircraft 200 is in service 112 and/or during maintenance and service 114 in FIG. 1.

The use of a number of the different advantageous embodiments may substantially expedite the assembly of and/or reduce the cost of aircraft 200. For example, the different advantageous embodiments may be used to test display systems during different phases in aircraft manufacturing and service method 100. For example, the display systems may be tested during specification and design 102 when manufacturing aircraft 200. Further, these display systems may be tested during routine maintenance and service 114. The testing may include existing systems as well as new systems that are installed during refurbishment or reconfiguration of aircraft 200. Of course, testing of display systems may occur during any operation in aircraft manufacturing and service method 100.

The different advantageous embodiments recognize and take into account a number of different considerations. For example, the different advantageous embodiments recognize and take into account that it is important for a human operator, such as a pilot of an aircraft, to have confidence in the information being displayed on a display device. A loss of confidence may result in the pilot making inaccurate decisions, taking additional time to verify information from other sources, and/or other actions that may result in a less than desirable operation of the aircraft.

The different advantageous embodiments recognize and take into account that with the use of display systems to display information, testing of the display systems may be performed on the display device. Testing may be performed to ensure that the display systems perform as desired under different operating conditions for the vehicle. Testing may be performed by having a person watch information displayed on a display device. This person may be referred to as a human analyst or just an analyst.

This type of testing may occur for hours at a time and over different days. The different advantageous embodiments recognize and take into account that this type of testing may be expensive with respect to the cost of people needed to watch the displays and determine whether undesired changes occur.

The different advantageous embodiments recognize and take into account that the testing of a display device may involve noting the current information being displayed on the display device. The process may involve changing a parameter and checking for the change on the display device. This change may include introducing an event at a test point in the vehicle to determine whether an undesired change in the display of information occurs on the display device.

The different advantageous embodiments recognize and take into account that using a person to look for these changes may be prone to error. The person may miss intermittent changes or may not notice a momentary blanking of the display. This type of error may occur due to the long durations of testing that occur. For example, testing of a display device may be performed for days, weeks, or even months, to determine whether undesired changes in a display of information occurs. Further, with different types of displays, the time and effort needed to test these other displays also increases.

Thus, the different advantageous embodiments provide a method and apparatus for testing a number of display devices. Images displayed on the number of display devices by a computer system for a platform are received, while a number of tests are performed in a number of test locations for the platform. The process identifies a portion of the images from the images as a number of images of interest using a policy.

Figure 3:
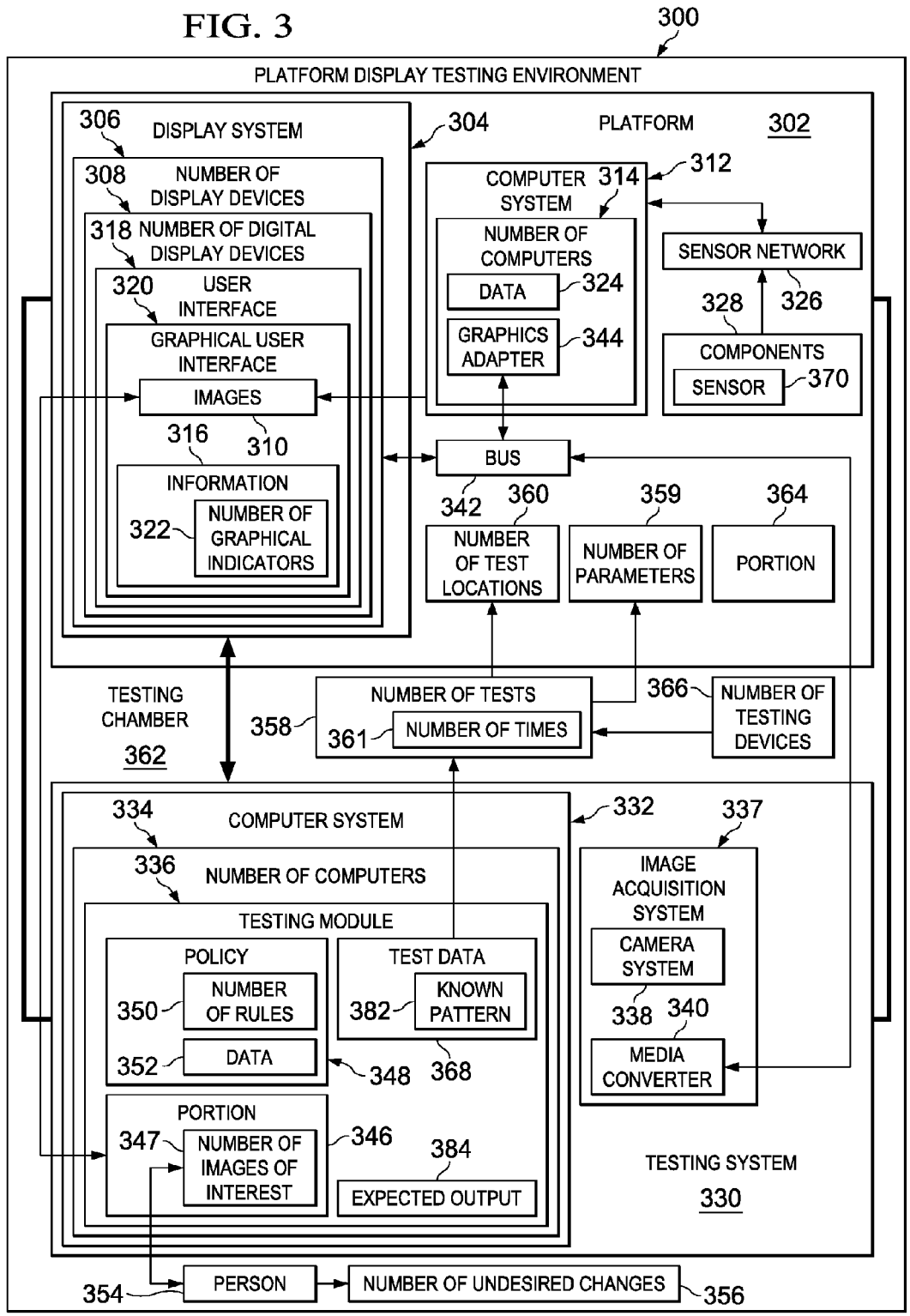
FIG. 3 is an illustration of a platform display testing environment in accordance with an advantageous embodiment.

With reference now to FIG. 3, an illustration of a platform display testing environment is depicted in accordance with an advantageous embodiment. Platform display testing environment 300 may be implemented to test platform 302. In these illustrative examples, platform 302 may be implemented using aircraft 200 in FIG. 2.

In particular, platform display testing environment 300 may be implemented to test display system 304 associated with platform 302. A first component, such as display system 304, may be considered to be associated with a second component, such as platform 302, by being secured, attached, bonded, fastened, and/or mounted to the second component. Further, the first component may be associated with the second component by being connected to the second component in some other suitable manner. Still further, the first component also may be connected to the second component by using a third component. The first component may also be considered to be associated with the second component by being formed as part of and/or an extension of the second component.

In these illustrative examples, display system 304 is located inside platform 302. Display system 304 comprises number of display devices 306. Number of display devices 306 is number of digital display devices 308 in these examples.

Number of digital display devices 308 displays information using pixels in these examples. Digital display devices may include, for example, without limitation, plasma displays, liquid crystal displays, organic light emitting diode displays, and/or other types of display devices on which graphics may be displayed. In other words, number of digital display devices 308 does not include an analog device, a physical gauge or instrument, or any display device that does not use graphics.

In these illustrative examples, number of display devices 306 displays images 310 generated by computer system 312. Computer system 312 is also associated with platform 302 and is located inside platform 302 in these examples. Computer system 312 comprises number of computers 314. Number of computers 314 is in communication with each other in these illustrative examples.

In particular, graphics adapter 344 located in computer system 312 generates images 310 under the control of computer system 312. Graphics adapter 344 is any hardware that generates images 310 under the control of computer system 312 in these examples. In other illustrative examples, graphics adapter 344 may be located in display system 304 or in other locations, depending on the particular implementation, while being controlled by computer system 312 to generate images.

Computer system 312 generates images 310 to display information 316 on number of display devices 306. As depicted, information 316 is displayed on number of display devices 306 using user interface 318. In particular, user interface 318 takes the form of graphical user interface 320. In these examples, information 316 is displayed graphically in images 310 on graphical user interface 320 as presented by number of display devices 306 in display system 304. Information 316 may be presented in the form of number of graphical indicators 322. Each graphical indicator may represent an instrument or a portion of an instrument for platform 302.

In these illustrative examples, computer system 312 receives data 324 from sensor network 326 associated with platform 302. Data 324 is processed by computer system 312 to generate information 316 for display on display system 304.

In these illustrative examples, sensor network 326 monitors components 328 in platform 302. These components may include, for example, without limitation, a lighting system, an environmental system, an entertainment system, an actuator system, a sensor, a flight control surface, a propulsion system, or some other suitable type of component. In these illustrative examples, components 328, sensor network 326, and computer system 312 may be connected to each other using wires in a wiring harness in which electrical signals and/or power is sent.

Testing system 330 is connected to display system 304 in these illustrative examples. As used herein, when a first component, such as testing system 330, is connected to a second component, such as display system 304, the first component may be connected to the second component without any additional components. The first component also may be connected to the second component by one or more other components. For example, one electronic device may be connected to a second electronic device without any additional electronic devices between the first electronic device and the second electronic device. In some cases, another electronic device may be present between the two electronic devices connected to each other.

Testing system 330 comprises computer system 332 containing number of computers 334. Testing module 336 is located in computer system 332 and receives images 310 generated by computer system 312. Testing module 336 displays images 310 on display system 304 in this depicted example.

Testing module 336 may be implemented using program code, hardware, or a combination of the two. For example, testing module 336 may take the form of an application that runs on processor units in computer system 332. In yet other illustrative examples, testing module 336 may take the form of circuits. These circuits may be implemented in one or more integrated circuits. With this type of implementation, testing module 336 may be located in computer system 332 or may be in a separate device.

In these illustrative examples, testing module 336 may obtain images 310 using image acquisition system 337. Image acquisition system 337 is a hardware device in testing system 330 configured to capture or obtain images 310 generated for display on display system 304.

Image acquisition system 337 may obtain images 310 in a number of different ways. For example, at least one of camera system 338, media converter 340, and other suitable components for obtaining images 310 may be used to implement image acquisition system 337.

Camera system 338 may be positioned relative to number of display devices 306 to capture images 310. Media converter 340 may be connected to bus 342 between number of display devices 306 and graphics adapter 344. Bus 342 is a number of wires that connects number of display devices 306 to graphics adapter 344. In this manner, media converter 340 may obtain images 310 sent from computer system 312 through bus 342 to display system 304 for display.

Images 310 received by testing module 336 in computer system 332 may be stored and processed by testing module 336. Testing module 336 identifies portion 346 of images 310 as number of images of interest 347 in the depicted examples.

This identification of portion 346 is performed using policy 348. Policy 348 comprises number of rules 350. In the different illustrative examples, policy 348 also may include data 352. Policy 348 is used to identify when images in images 310 should be part of portion 346 for further analysis. Further, number of rules 350 and data 352 in policy 348 may be used to identify when images, between which changes are present, are to be included in number of images of interest 347.

Number of images of interest 347 in portion 346 may be analyzed by person 354 to determine whether number of undesired changes 356 has occurred in the display of images 310 on number of display devices 306 in display system 304. In other words, person 354 looks at each image in number of images of interest 347 in portion 346 to determine whether any of the changes between images are number of undesired changes 356. In these illustrative examples, this determination may be subjective based on the experience of person 354, a policy used by person 354, and/or any other suitable metric. In these illustrative examples, person 354 may be a vehicle operator, a programmer, a pilot, or some other suitable person.

In these illustrative examples, images 310 are generated by computer system 312 during operation of platform 302. The operation of platform 302 also may include performing number of tests 358 in number of test locations 360 for platform 302. In other words, number of tests 358 is performed during the generation of images 310 in these illustrative examples. Number of tests 358 may be testing events or situations that may occur during operation of platform 302 under different operating conditions.

Number of tests 358 may be selected to determine whether changes in operating conditions in platform 302 may cause number of undesired changes 356 in images 310 generated by computer system 312. Number of undesired changes 356 may be caused by number of tests 358 in a manner that data 324 may be affected as data 324 is transmitted over wires in platform 302.

Number of tests 358 may change number of parameters 359 in platform 302. The change in number of parameters 359 may cause changes in operating conditions in platform 302. In these illustrative examples, the changes in number of parameters 359 may include, for example, at least one of changing a current in a component, introducing radio frequency signals to a component, applying an electrical discharge to platform 302, and/or other suitable types of changes.

In still other illustrative examples, number of undesired changes 356 may be caused by changes in the operation of components 328 in platform 302. In yet other illustrative examples, number of undesired changes 356 in images 310 may be caused by the effects of number of tests 358 on at least one of computer system 312, display system 304, and/or other components in platform 302. In other words, number of undesired changes 356 is any undesired change to the display of information 316 in images 310 on number of display devices 306 from any source associated with platform 302.

Additionally, number of times 361 for number of tests 358 may be sent to and stored in computer system 312. A time within number of times 361 is a time at which a test within number of tests 358 was performed. The time may include a starting time, a stopping time, and/or a period of time during which the test was performed.

Number of times 361 may be used to correlate or identify which tests in number of tests 358 may be the cause of number of undesired changes 356. Further, number of test locations 360 also may be stored with number of times 361.

In these illustrative examples, with portion 346, person 354 may review less than all of images 310 in determining whether number of undesired changes 356 is present. As a result, the amount of time needed by person 354 to identify number of undesired changes may be reduced. For example, reviewing images for hundreds of hours may be reduced to reviewing images generated over a few minutes or a few hours.

In the different illustrative examples, platform 302 may be tested using testing system 330 in testing chamber 362. In the different illustrative examples, the testing of platform 302 may involve placing portion 364 or all of platform 302 in testing chamber 362. In some illustrative examples, portion 364 of platform 302 may be assembled for testing. In other words, portion 364 of platform 302 may be placed in or built inside of testing chamber 362 in the different illustrative examples.

In other examples, testing system 330 may not require testing chamber 362. In the illustrative examples, testing system 330 also may include number of testing devices 366. Number of testing devices 366 is used to perform number of tests 358 in these illustrative examples.

In these illustrative examples, test data 368 may be introduced into components 328. For example, components 328 may include sensor 370. Test data 368 may be generated by testing module 336 in these examples. Test data 368 may be considered a parameter that changes in number of parameters 359. Test data 368 may be, for example, known pattern 382. With known pattern 382, images 310 should include expected output 384. Expected output 384 is an output that is expected to be displayed in number of display devices 306 in response to known pattern 382. In other words, expected output 384 is expected to be present in images 310.

Number of tests 358 may cause changes such that expected output 384 does not occur when known pattern 382 is input into sensor 370. In a similar fashion, other components may be tested using test data 368 in which expected output 384 is expected to be displayed on number of display devices 306.

With this type of testing, if changes from expected output 384 vary more than a desired amount, then those images may be included in portion 346 as number of images of interest 347. The amount of change from expected output 384 that may be acceptable is set using policy 348.

In one illustrative example, known pattern 382 may be sent into a wiring harness in components 328. As a result, individual components or entire systems may be tested with respect to images 310 displayed on number of display devices 306.

In still other illustrative examples, images 310 may be compared with each other to identify changes between images 310. The amount of change between images in images 310 that cause those images to be included in portion 346 as number of images of interest 347 may also be set using policy 348.

Further, errors in identifying number of undesired changes 356 may be reduced because of a reduced amount of images 310 being reviewed by person 354. As a result, issues with fatigue and missing changes over long periods of time may be reduced.

Thus, the different advantageous embodiments reduce the amount of time needed by person 354 to identify number of undesired changes 356 in images 310 through only reviewing portion 346 of images 310. In this manner, the amount of time and effort needed to test display system 304 may be reduced.

The illustration of platform display testing environment 300 in FIG. 3 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, although aircraft 200 in FIG. 2 is an example of an implementation of platform 302, the different advantageous embodiments also recognize that some advantageous embodiments may be applied to other types of platforms. For example, without limitation, other advantageous embodiments may be applied to a mobile platform, a stationary platform, a land-based structure, an aquatic-based structure, a space-based structure, and/or some other suitable object. More specifically, the different advantageous embodiments may be applied to, for example, without limitation, a submarine, a bus, a personnel carrier, a tank, a train, an automobile, a spacecraft, a space station, a satellite, a surface ship, a power plant, a dam, a manufacturing facility, a building, and/or some other suitable object.

As yet another example, although person 354 reviews portion 346 of images 310 for number of undesired changes 356, this review may be performed in other ways. For example, an artificial intelligence program may be used to identify number of undesired changes 356 within portion 346 of images 310.

Although the illustrative examples may be applied to testing displays in a controlled or test situation, platform display testing environment 300 may be applied to other types of situations. For example, platform display testing environment 300 may be applied to testing displays for platforms during actual operation of a platform. In this example, the images are displayed during performance of an operation by an operator and used to perform the operation. The operator may be an operator of an aircraft such as, for example, an unmanned aircraft or a manned aircraft.

For example, platform 302 may take the form of an unmanned aerial vehicle control system, an aircraft, or some other suitable type of platform. With an unmanned aerial vehicle control system, images 310 may be generated by unmanned aerial vehicles and sent to the unmanned aerial vehicle control system. An unmanned aerial vehicle control system, in these examples, controls multiple unmanned aerial vehicles. With this type of embodiment, testing module 336 and image acquisition system 337 are both located on platform 302 with number of display devices 306. In this example, person 354 is an operator of platform 302.

In this particular example, images 310 are viewed by an operator of the unmanned aerial vehicle control system. The operator uses images 310 to control the unmanned aerial vehicles. The operator of the unmanned aerial vehicle control system may select targets using images 310.

Number of images of interest 347 may be displayed on a display device in the unmanned aerial vehicle control system. The operator may look at number of images of interest 347 to determine whether number of undesired changes 356 have occurred. If number of undesired changes 356 has occurred, the operator of the unmanned aerial vehicle control system may decide to reselect the target that was selected when number of undesired changes 356 occurred in images 310 and/or perform some other suitable operation.

In a similar fashion, a pilot of an aircraft may track multiple targets. The pilot may select targets one after another. The aircraft may be configured to fire weapons on the selected targets at a later time. In this particular example, the operation performed by the operator is for the aircraft to perform an action at a future time after the operation is performed. Testing module 336 may be configured to display number of images of interest 347 before the action occurs in the future time.

In this example, images 310 are displayed on number of display devices 306 in the aircraft. Images 310 displayed on number of display devices 306 may provide information, such as an identification of targets on a radar system.

With this type of environment, testing module 336 may identify number of images of interest 347 from images 310 that have been generated. Number of images of interest 347 may be displayed to the pilot while the pilot is still selecting targets and/or after the pilot has finished selecting targets.

The pilot may then determine whether number of undesired changes 356 may have occurred. If number of undesired changes 356 occurred during the selection of a particular target, the pilot may then cancel that selection and reselect the target and/or perform some other suitable operation.

In these examples, testing of number of display devices 306 occurs during actual operation outside of testing of the unmanned aerial vehicle control system and the aircraft. The identification of number of images of interest 347 may provide an operator of the unmanned aerial vehicle control system and the aircraft an ability to determine whether operations performed using images may need to be changed. This change may include re-performing the operation, canceling the operation, or performing some other action with respect to the operation performed when number of undesired changes 356 is identified in number of images of interest 347.

In this manner, the different advantageous embodiments may be used during testing and/or actual operation of the unmanned vehicle control system. During testing, identification of issues that may be present in the use of number of display devices 306 may be identified. The identification of these issues may be used to make changes to platform 302. During operation of platform 302 outside of testing, the identification of number of undesired changes 356 may be used to determine whether to make changes to operations performed using platform 302.

Figure 4:
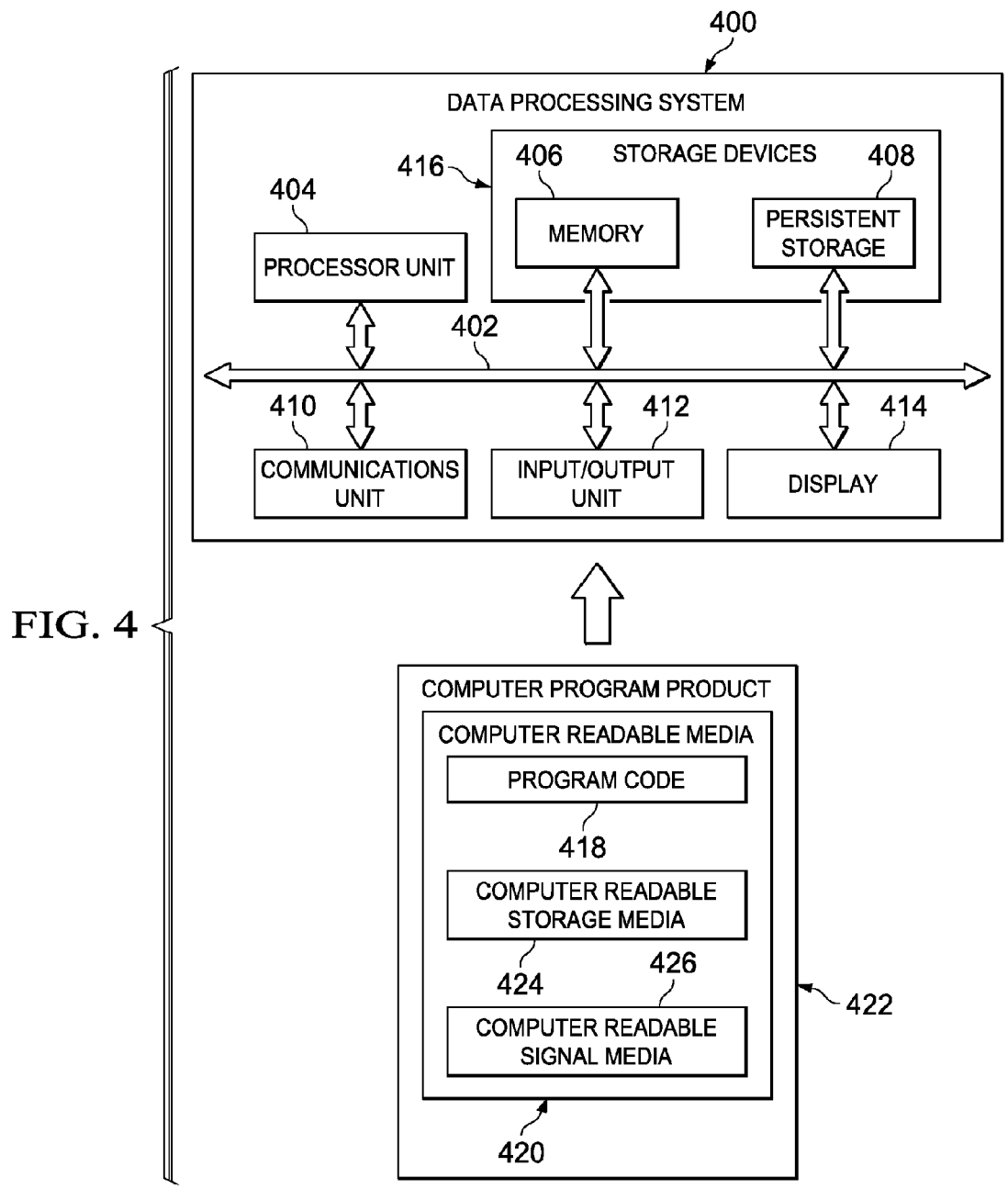
FIG. 4 is an illustration of a data processing system in accordance with an advantageous embodiment.

Turning now to FIG. 4, an illustration of a data processing system is depicted in accordance with an advantageous embodiment. In this illustrative example, data processing system 400 includes communications fabric 402, which provides communications between processor unit 404, memory 406, persistent storage 408, communications unit 410, input/output (I/O) unit 412, and display 414. Data processing system 400 is an example of a data processing system that may be used to implement number of computers 314 in computer system 312 in FIG. 3. In addition, data processing system 400 also may be used to implement number of computers 334 in computer system 332 in FIG. 3.

Processor unit 404 serves to execute instructions for software that may be loaded into memory 406. Processor unit 404 may be a number of processors, a multi-processor core, or some other type of processor, depending on the particular implementation. A number, as used herein with reference to an item, means one or more items. Further, processor unit 404 may be implemented using a number of heterogeneous processor systems in which a main processor is present with secondary processors on a single chip. As another illustrative example, processor unit 404 may be a symmetric multi-processor system containing multiple processors of the same type.

Memory 406 and persistent storage 408 are examples of storage devices 416. A storage device is any piece of hardware that is capable of storing information, such as, for example, without limitation, data, program code in functional form, and/or other suitable information either on a temporary basis and/or a permanent basis. Storage devices 416 may also be referred to as computer readable storage devices in these examples. Memory 406, in these examples, may be, for example, a random access memory or any other suitable volatile or non-volatile storage device. Persistent storage 408 may take various forms, depending on the particular implementation.

For example, persistent storage 408 may contain one or more components or devices. For example, persistent storage 408 may be a hard drive, a flash memory, a rewritable optical disk, a rewritable magnetic tape, or some combination of the above. The media used by persistent storage 408 also may be removable. For example, a removable hard drive may be used for persistent storage 408.

Communications unit 410, in these examples, provides for communications with other data processing systems or devices. In these examples, communications unit 410 is a network interface card. Communications unit 410 may provide communications through the use of either or both physical and wireless communications links.

Input/output unit 412 allows for input and output of data with other devices that may be connected to data processing system 400. For example, input/output unit 412 may provide a connection for user input through a keyboard, a mouse, and/or some other suitable input device. Further, input/output unit 412 may send output to a printer. Display 414 provides a mechanism to display information to a user.

Instructions for the operating system, applications, and/or programs may be located in storage devices 416, which are in communication with processor unit 404 through communications fabric 402. In these illustrative examples, the instructions are in a functional form on persistent storage 408. These instructions may be loaded into memory 406 for execution by processor unit 404. The processes of the different embodiments may be performed by processor unit 404 using computer implemented instructions, which may be located in a memory, such as memory 406.

These instructions are referred to as program code, computer usable program code, or computer readable program code that may be read and executed by a processor in processor unit 404. The program code in the different embodiments may be embodied on different physical or computer readable storage media, such as memory 406 or persistent storage 408.

Program code 418 is located in a functional form on computer readable media 420 that is selectively removable and may be loaded onto or transferred to data processing system 400 for execution by processor unit 404. Program code 418 and computer readable media 420 form computer program product 422 in these examples. In one example, computer readable media 420 may be computer readable storage media 424 or computer readable signal media 426. Computer readable storage media 424 may include, for example, an optical or magnetic disk that is inserted or placed into a drive or other device that is part of persistent storage 408 for transfer onto a storage device, such as a hard drive, that is part of persistent storage 408.

Computer readable storage media 424 also may take the form of a persistent storage, such as a hard drive, a thumb drive, or a flash memory, that is connected to data processing system 400. In some instances, computer readable storage media 424 may not be removable from data processing system 400. In these examples, computer readable storage media 424 is a physical or tangible storage device used to store program code 418, rather than a medium that propagates or transmits program code 418. Computer readable storage media 424 is also referred to as a computer readable tangible storage device or a computer readable physical storage device. In other words, computer readable storage media 424 is a media that can be touched by a person.

Alternatively, program code 418 may be transferred to data processing system 400 using computer readable signal media 426. Computer readable signal media 426 may be, for example, a propagated data signal containing program code 418. For example, computer readable signal media 426 may be an electromagnetic signal, an optical signal, and/or any other suitable type of signal.

In some advantageous embodiments, program code 418 may be downloaded over a network to persistent storage 408 from another device or data processing system through computer readable signal media 426 for use within data processing system 400. For instance, program code stored in a computer readable storage medium in a server data processing system may be downloaded over a network from the server to data processing system 400. The data processing system providing program code 418 may be a server computer, a client computer, or some other device capable of storing and transmitting program code 418.

The different components illustrated for data processing system 400 are not meant to provide architectural limitations to the manner in which different embodiments may be implemented. The different advantageous embodiments may be implemented in a data processing system including components in addition to or in place of those illustrated for data processing system 400. Other components shown in FIG. 4 can be varied from the illustrative examples shown.

The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 404 may take the form of a hardware unit that has circuits that are manufactured or configured for a particular use. This type of hardware may perform operations without needing program code to be loaded into a memory from a storage device to be configured to perform the operations.

For example, when processor unit 404 takes the form of a hardware unit, processor unit 404 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, programmable array logic, a field programmable logic array, a field programmable gate array, and other suitable hardware devices. With this type of implementation, program code 418 may be omitted, because the processes for the different embodiments are implemented in a hardware unit.

In still another illustrative example, processor unit 404 may be implemented using a combination of processors found in computers and hardware units. Processor unit 404 may have a number of hardware units and a number of processors that are configured to run program code 418. With this depicted example, some of the processes may be implemented in the number of hardware units, while other processes may be implemented in the number of processors.

In another example, a bus system may be used to implement communications fabric 402 and may be comprised of one or more buses, such as a system bus or an input/output bus. Of course, the bus system may be implemented using any suitable type of architecture that provides for a transfer of data between different components or devices attached to the bus system.

Additionally, a communications unit may include a number of devices that transmit data, receive data, or transmit and receive data. A communications unit may be, for example, a modem or a network adapter, two network adapters, or some combination thereof. Further, a memory may be, for example, memory 406, or a cache, such as found in an interface and memory controller hub that may be present in communications fabric 402.

Figure 5:
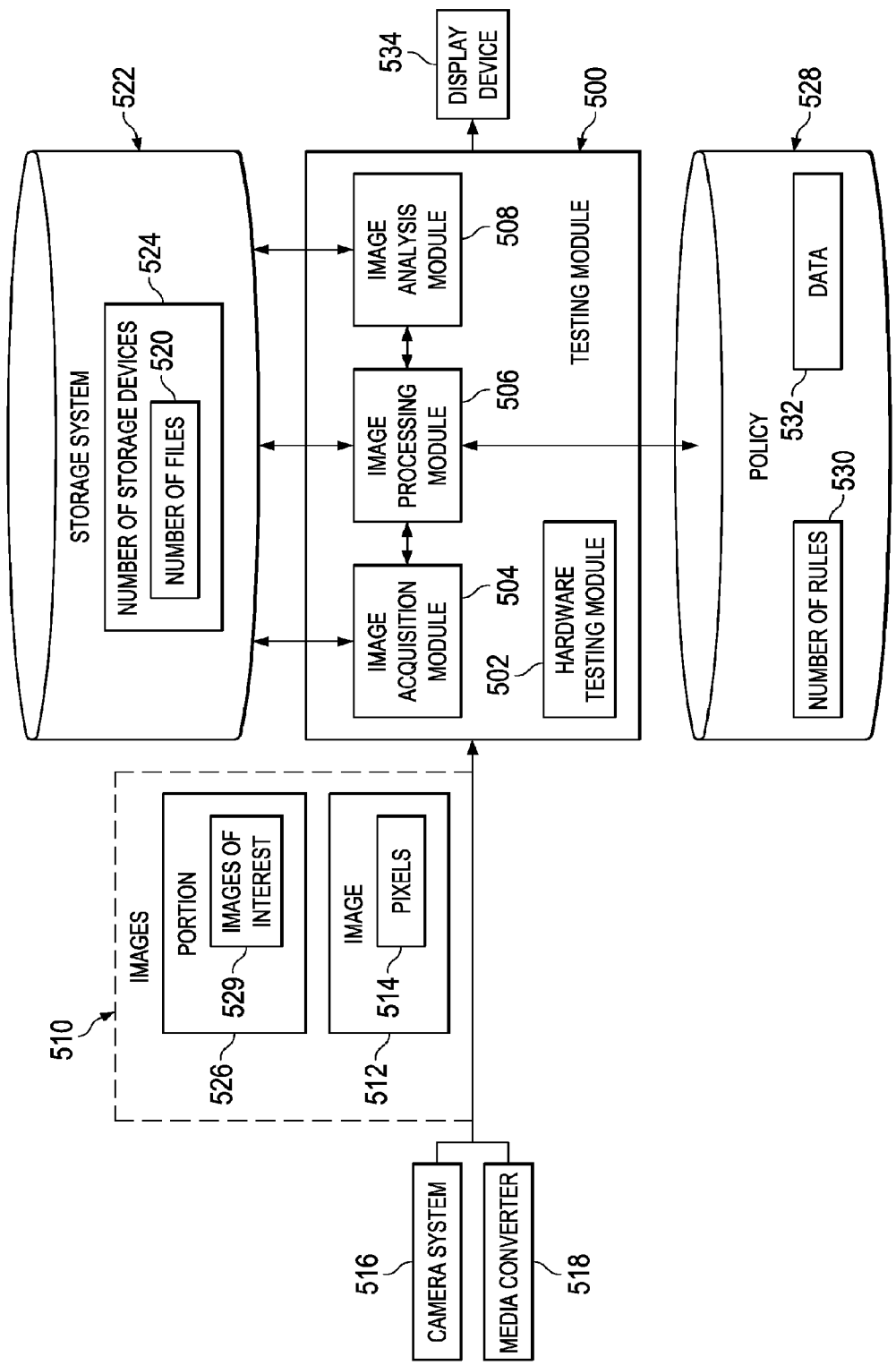
FIG. 5 is an illustration of a testing module in accordance with an advantageous embodiment.

With reference now to FIG. 5, an illustration of a testing module is depicted in accordance with an advantageous embodiment. Testing module 500 is an example of one implementation for testing module 336 in FIG. 3. Testing module 500 may be implemented in software, hardware, or a combination of the two. When implemented in hardware, testing module 500 takes the form of hardware testing module 502. In other words, the different processes for operations performed by hardware testing module 502 are implemented in hardware. In some cases, a portion of the operations also may be implemented using software.

In this illustrative example, testing module 500 comprises a number of different modules. For example, testing module 500 includes image acquisition module 504, image processing module 506, and image analysis module 508.

Image acquisition module 504 is configured to receive images 510 or images generated by hardware for display on a display device, such as number of display devices 306 in FIG. 3. In these illustrative examples, an image, such as image 512 in images 510, comprises pixels 514. Image acquisition module 504 is connected to at least one of camera system 516, media converter 518, and other suitable hardware for obtaining images 510.

In these examples, image acquisition module 504 stores images 510 in storage system 522. Storage system 522 comprises number of storage devices 524. Each storage device in number of storage devices 524 is configured to store images 510 in a digital form. Number of storage devices 524 may be in the same location or spread out through different locations. Number of storage devices 524 may take different forms, such as hard drives, optical disk drives, and other suitable types of storage devices.

Image processing module 506 is configured to identify portion 526 of images 510 in number of files 520. Portion 526 is identified using policy 528 in these illustrative examples. Portion 526 comprises images of interest 529.

Policy 528 may comprise number of rules 530 and data 532. Number of rules 530 is used to identify portion 526 of images 510 for further analysis. In these illustrative examples, image analysis module 508 is configured to display portion 526 of images 510 identified by image processing module 506. In these illustrative examples, image analysis module 508 may display portion 526 on display device 534 to a human analyst.

Image analysis module 508 may be configured to allow the human analyst to manipulate the display of portion 526. In other words, the human analyst may review images of interest 529 within portion 526 individually, in real time, and/or at different speeds. Of course, image analysis module 508 also may allow for other types of manipulations of images of interest 529, depending on the particular implementation.

Further, image analysis module 508 also may be configured to allow the human analyst to make notes, annotations, and generate other input with respect to portion 526 of images 510. The user input may include, for example, identifying undesired changes within images of interest 529. These undesired changes may be identified using a policy, rules, or other guidelines that may be selected for identifying these types of undesired changes.

Further, the times at which images of interest 529 were generated may be correlated with any tests being performed on the platform. This type of correlation may allow for identifying undesired changes in the images. Further, a source of the undesired changes also may be identified based on this type of correlation.

The illustration of testing module 500 in FIG. 5 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, testing module 500 may be located on the same computer or a different computer in a computer system. Further, different components in testing module 500 may be located on different computer systems, depending on the particular implementation. For example, hardware testing module 502 may be located on one computer, while image acquisition module 504 is located on a different computer. In still other illustrative examples, image processing module 506 may be located on yet another computer.

Further, in some illustrative examples, the functions for hardware testing module 502 and image acquisition module 504 may be located in a single module rather than separate modules, depending on the particular implementation. In other words, the description of the different functions for the different modules does not imply that the modules are always implemented as separate software or hardware components. As another example, in some cases, all of images 510 also may be stored on number of storage devices 524. In this type of implementation, images of interest 529 in portion 526 may be marked or identified for review.

Figure 6:
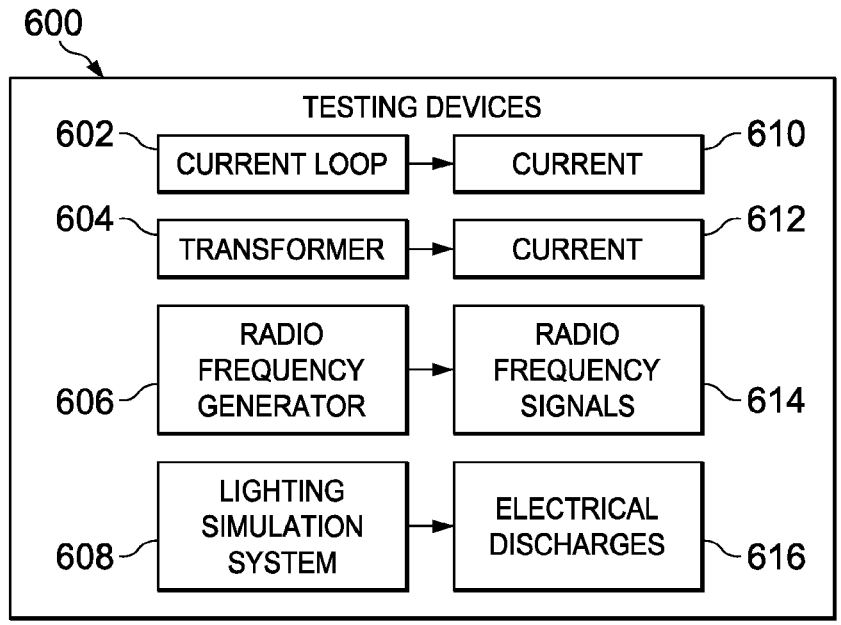
FIG. 6 is an illustration of testing devices in accordance with an advantageous embodiment.

With reference now to FIG. 6, an illustration of testing devices is depicted in accordance with an advantageous embodiment. Testing devices 600 illustrate devices that may be used in number of testing devices 366 in FIG. 3.

Testing devices 600 include devices configured to introduce interference to platform 302 in FIG. 3. This interference may be anything that may change the operation of platform 302 such that images 310 displayed on number of display devices 306 on platform 302 in FIG. 3 are altered in an undesired manner. For example, testing devices 600 may include current loop 602, transformer 604, radio frequency generator 606, lightning simulation system 608, and any other suitable types of testing devices.

Current loop 602 generates current 610. Current 610 may be used to induce current changes in wires or systems within a platform. Transformer 604 induces current 612 in different systems. Changes in currents 610 and 612 may simulate power fluctuations, changes in loads, and/or other events that may occur during the operation of platform 302 in FIG. 3 that may interfere with the operation of platform 302.

Radio frequency generator 606 may generate radio frequency signals 614 that may generate radio frequency interference. These radio frequency signals may be directed at various components within platform 302. For example, radio frequency generator 606 may be a signal generator connected to an antenna.

A mobile phone or some other device also may be used as an example of an implementation of radio frequency generator 606 in determining the effects of radio frequency signals on different components in platform 302 during normal operation of platform 302. For example, different passengers or users may operate mobile phones within or near platform 302. As one illustrative example, these mobile phones may affect radio navigation by affecting, for example, without limitation, radio altimeter readings, glide slope, very high frequency (VHF) omnidirectional range (VOR) systems, an instrument landing system (ILS), and/or other radio navigation systems on platform 302.

Lightning simulation system 608 is configured to simulate electrical discharges 616 that may be applied to platform 302 during operation of platform 302. Lightning simulation system 608 may be implemented using various systems. For example, a Thermo Scientific ECAT Lightning Test System available from Thermo Fischer Scientific, Inc. in Waltham, Mass. may be used.

The illustration of testing devices 600 in FIG. 6 is not meant to imply limitations to the number or types of testing devices that may be used in number of testing devices 366 in FIG. 3. For example, a testing device to simulate an electrical magnetic pulse, heat, impacts, and other events may be used in number of testing devices 366 in FIG. 3.

Testing devices 600 may be used in number of test locations 360 in FIG. 3 to perform number of tests 358. Number of tests 358 may be performed in number of test locations 360 to determine whether number of undesired changes 356 occurs in images 310 when images 310 are generated by computer system 312 during the performance of number of tests 358 on platform 302.

Figure 7:
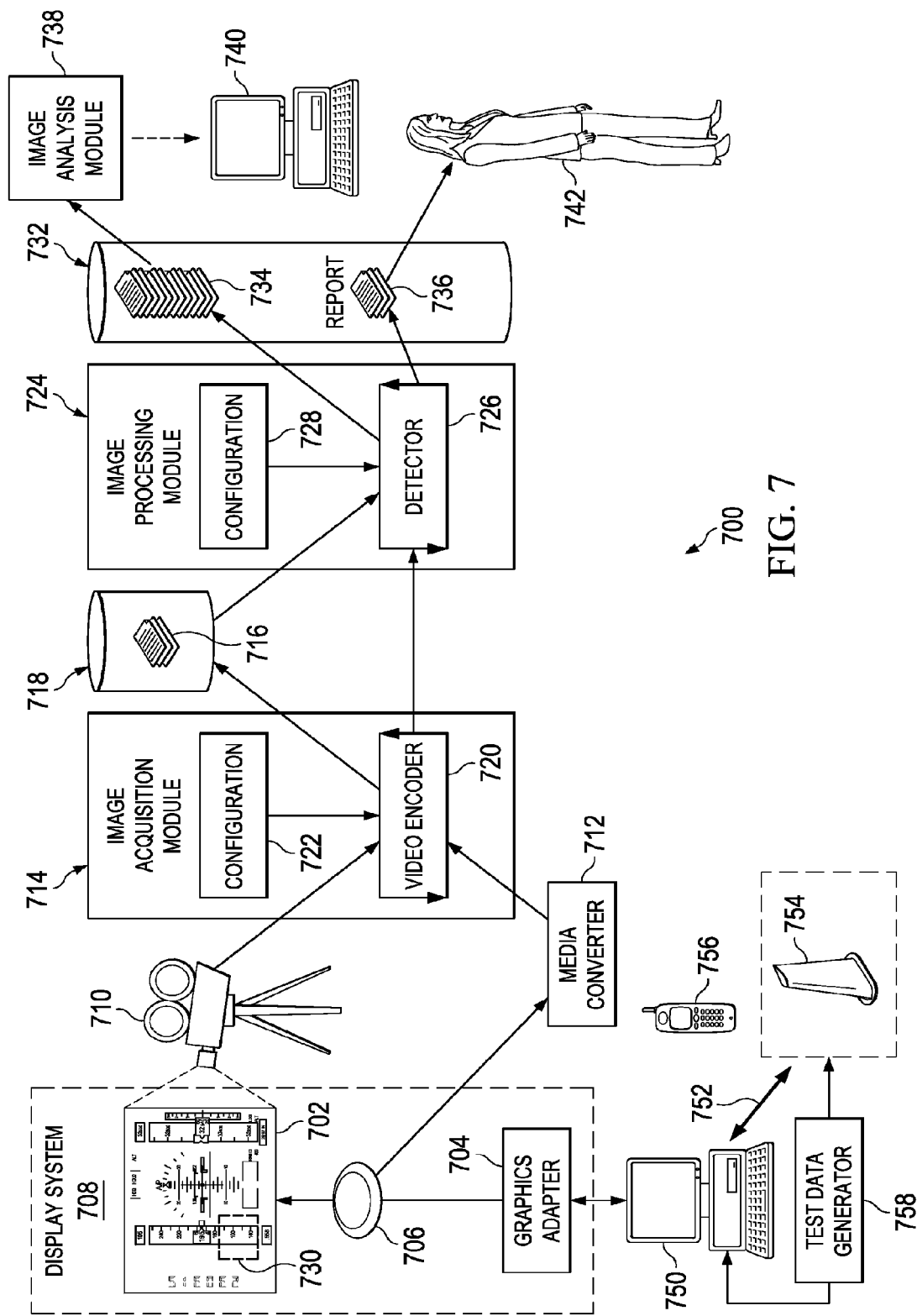
FIG. 7 is an illustration of a platform testing environment in accordance with an advantageous embodiment.

With reference now to FIG. 7, an illustration of a platform testing environment is depicted in accordance with an advantageous embodiment. In this illustrative example, platform display testing environment 700 is an example of one implementation for platform display testing environment 300 in FIG. 3.

In this illustrative example, display device 702 is connected to graphics adapter 704 by bus 706. Display device 702, graphics adapter 704, and bus 706 are part of a display system for a platform that is being tested.

Camera 710 and media converter 712 generate images for processing by image acquisition module 714. Images sent to image acquisition module 714 may be processed and stored in video files 716 in storage device 718.

Camera 710 may be a video camera configured to generate images while information is displayed on display device 702. Camera 710 may be mounted in front of or connected to display device 702 in a manner that provides a desired quality for the images generated by camera 710.

For example, camera 710 may be positioned such that the amount of noise in capturing images from display device 702 may be reduced. In these examples, a change in light may cause noise in the generation of images by camera 710. In one example, light in the room and movement of people in the room may cause changes in the manner in which light falls on display device 702. A shroud or cover may be placed over display device 702 and camera 710 to reduce noise in some illustrative examples.

As depicted, media converter 712 may be connected to bus 706. This type of image acquisition may reduce noise concerns by obtaining data for the images directly from graphics adapter 704.

In this illustrative example, image acquisition module 714 includes video encoder 720 and configuration 722. Video encoder 720 is configured to change data generated by camera 710 and media converter 712 into a format for processing. This type of processing is also referred to as encoding or video conversion. The format allows for the images to be played back by different types of recorders that are configured to play video files in that particular format. Additionally, video encoder 720 also may add timestamps to each of the images.

Video files 716 are processed by image processing module 724 to identify images of interest. In these illustrative examples, image processing module 724 includes detector 726 and configuration 728. In these illustrative examples, configuration 728 may include various parameters for processing images by video encoder 720. For example, without limitation, configuration 728 may include video resolution, video encoding compression format, storage path, and/or other suitable information.

Detector 726 is configured to identify a portion of the images in video files 716 that have changes that are sufficient to identify the portion of the images as being images of interest. In other words, a change from one image to another image may be so sufficient that the image in which the change occurred is identified as an image of interest.

Further, this portion also may include some number of images prior to and/or after the image of interest. The inclusion of these images may provide contacts for determining whether the image of interest contains an undesired change. Configuration 728 specifies whether a change is sufficient enough to identify an image as an image of interest.

In these illustrative examples, configuration 728 may identify a percentage of pixels that change, an amount of change in intensity, a change in colors, and/or other metrics that may be used to determine whether the change is sufficient to identify an image with the change as an image of interest. These values may be referred to as thresholds.

In these illustrative examples, the processing of images in video files 716 may be made faster by number of areas 730 on display device 702 defined by configuration 728. Number of areas 730 is one or more areas on display device 702 that may be of interest. For example, certain areas on display device 702 may display information that may cause a loss in confidence in the display of the information by display device 702 if changes occurred in those areas.

Detector 726 may compare number of areas 730 from one image to number of areas 730 in another image in video files 716 to determine whether changes are sufficient to identify one or both of the images as an image of interest. This undesired change may be defined in a number of different ways. For example, the change may be between an area in a first image and the area in a second image preceding the first image. The second image that precedes the first image is the image just prior to the first image in a sequence of images without any other images in between the first image and the second image, in this particular example, for one advantageous embodiment.

The results of processing video files 716 are stored in storage device 732. In these illustrative examples, images 734 are images of interest. Additionally, detector 726 also generates report 736. Report 736 includes images that contain undesired changes.

Additionally, reports 736 also may include information, such as the total number of images, the total number of times undesired changes were detected, the duration of the video for the images, thresholds used, and/or other suitable types of information.

In these illustrative examples, image analysis module 738 is configured to display images 734 on display device 740. Person 742 may view and annotate images 734 displayed on display device 740. Person 742 reviews images 734 and may identify one or more of these images as having undesired changes. In this example, person 742 is an analyst. Those images having undesired changes may be identified and marked by person 742.

Further, in these illustrative examples, image analysis module 738 may also be configured to display graphical indicators in association with particular areas on images 734. This display of these graphical indicators indicates the areas on images 734 where changes sufficient to identify the images as images of interest were detected.

In this manner, person 742 may be able to more easily view areas on images 734 where undesired changes may be present. In other words, person 742 may analyze the areas on images 734 associated with graphical indicators to identify undesired changes rather than analyzing all of images 734. Further, person 742 may be able to annotate images 734 to indicate whether undesired changes are actually present in the areas indicated by the graphical indicators.

In these illustrative examples, the operation of display system 708 and the acquisition of images by image acquisition module 714 occur during the performance of a number of tests. In these illustrative examples, computer system 750, wiring harness 752, and antenna 754 are examples of components in the platform. Computer system 750 controls graphics adapter 704 to create images for display on display device 702.

One or more of these components may be tested while images are generated and displayed on display device 702. For example, tests as to whether radio frequency (RF) signals may cause undesired changes in the images displayed on display device 702 may be performed. The generation of RF signals may be performed using a test device. This test device may be, for example, mobile phone 756. Mobile phone 756 may be operated to simulate usage of mobile phones by passengers or other people near components, such as computer system 750, wiring harness 752, and antenna 754.

A test device, such as mobile phone 756, may cause images 734 to deviate from the expected output. This type of change may indicate undesired changes in the images displayed in display device 702.

In yet other illustrative examples, test data may be introduced into different components. For example, test data generator 758 may be used to introduce test data into wiring harness 752 and/or antenna 754 in these illustrative examples. Test data generator 758 is any device capable of generating test data. This test data may take the form of test patterns or other information. With the test data, an expected output for the test data should be generated at display device 702.

With identification of the images having undesired changes, the time at which the images were generated may be correlated with tests being performed on the platform. In this manner, a particular component or components that may be the source of the undesired change can be identified. Further, different environmental factors or operating conditions being tested by the number of tests also may identify changes that may be needed to those components.

Alternatively, techniques or mechanisms to reduce the operating conditions or environmental conditions causing the undesired change may be identified. Although mobile phone 756 is shown as a test device, other test devices may be used to generate radio frequency signals. In addition, other types of test devices also may be used to perform other types of tests, depending on the particular implementation. Further, in some illustrative examples, test data generator 758 may not be used with mobile phone 756.

The illustration of platform display testing environment 700 is presented as one example implementation for platform display testing environment 300 in FIG. 3 and is not meant to imply physical or architectural limitations to the manner in which advantageous embodiments may be implemented. For example, in some examples, only one of camera 710 and media converter 712 may be used. In still other illustrative examples, additional display devices may be tested in addition to display device 702.

In these illustrative examples, the capturing of images is performed while testing in different locations on a platform is performed. These different locations may affect the manner in which images are generated by graphics adapter 704.

In other illustrative examples, display system 708, computer system 750, wiring harness 752, and antenna 754 may be components in a platform that are tested during actual operation of the platform. With this type of illustrative example, mobile phone 756 and test data generator 758 are not used. Display device 740 is located in the platform.

In some illustrative examples, person 742 may be an operator of the platform rather than a tester or analyst of display system 708. Person 742 may be, for example, without limitation, a pilot, a driver, a gunner, a fire support person, or some other suitable type of operator. With this type of implementation, person 742 uses display device 702 to operate the platform.

For example, person 742 may select targets and perform other operations. Images of interest are displayed on display device 740. Person 742 may review images of interest to determine whether operations performed by person 742 may need to be re-thought or re-analyzed.

For example, person 742 selects three targets one after another during a mission. Images of interest may be displayed on display device 740 with respect to images that were displayed on display device 702 when the second target was selected.

Person 742 may review the images of interest to determine whether an undesired change has occurred in the images. If an undesired change has occurred, person 742 may determine whether the operation performed in selecting the second target needs to be changed. For example, person 742 may change the operation in selecting the second target by canceling a selection, re-selecting a target, or forming some other suitable operation.

In yet other illustrative examples, a single storage device may be used instead of storage device 718 and storage device 732. As another example, when platform display testing environment 700 is used in actual operation of a platform, image acquisition module 714, image processing module 724, and image analysis module 738 may be implemented in hardware. In particular, these modules may be implemented in one or more integrated circuits that are associated with the platform.

Figure 8:
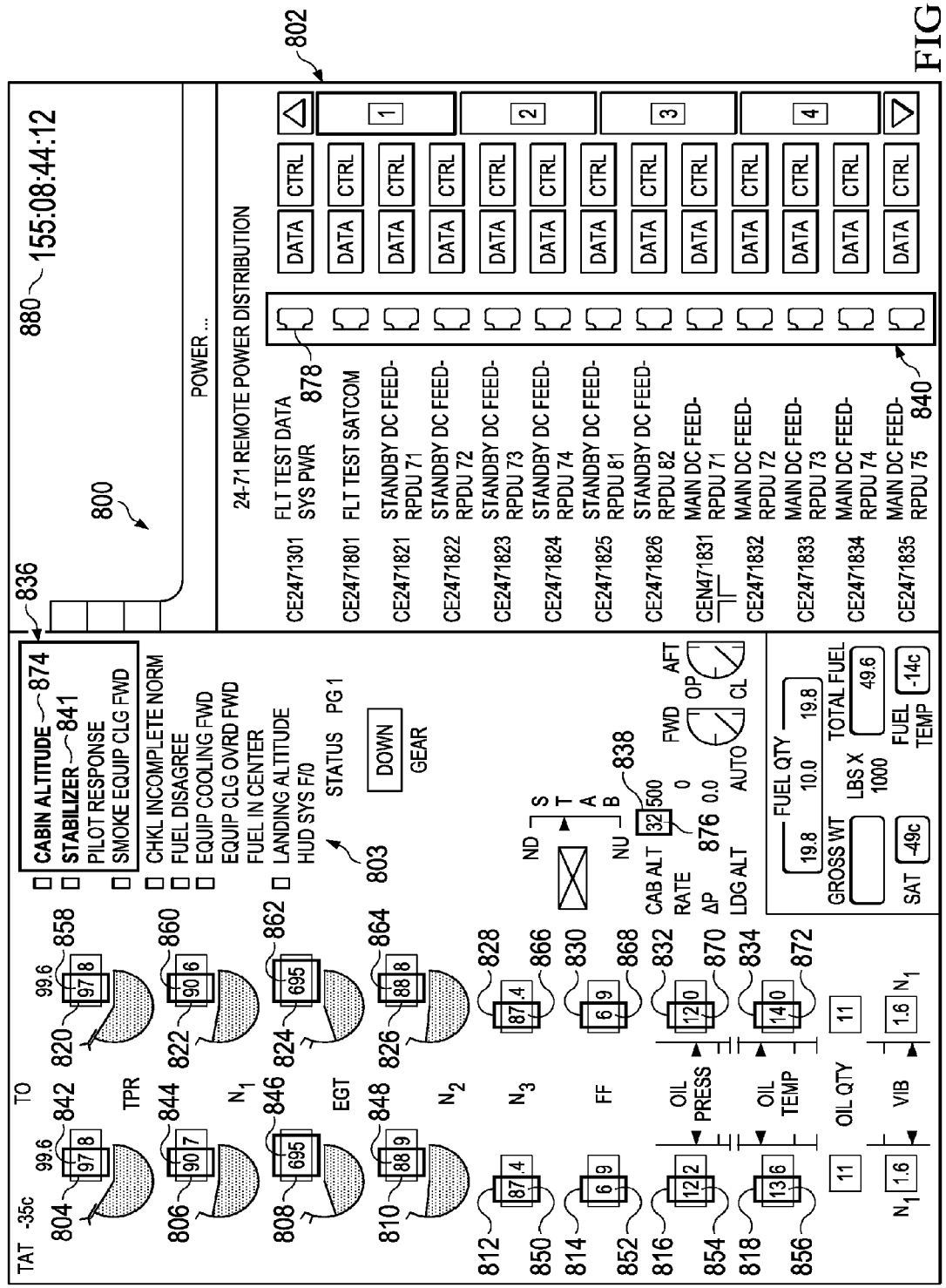
FIG. 8 is an illustration of an image displayed on a display device in accordance with an advantageous embodiment.

With reference now to FIG. 8, an illustration of an image displayed on a display device is depicted in accordance with an advantageous embodiment. In this illustrative example, image 800 displayed on display device 802 is an example of one implementation of an image in images 310 in FIG. 3 and/or images 510 in FIG. 5. Display device 802 is an example of one implementation for display device 534 in FIG. 5. Image 800 is displayed on display device 802 for viewing by a person at display device 802. The person may be, for example, an analyst.

In this illustrative example, image 800 is an initial image in a sequence of images that were analyzed for selecting images of interest. The sequence of images includes images that are captured using, for example, camera system 338 in FIG. 3 and/or camera system 516 in FIG. 5. In this illustrative example, image 800 is displayed on display device 802 as an image of interest for the person to view.

As depicted, graphical indicators 803 are displayed on image 800 in association with areas 841 on image 800. Graphical indicators 803 include graphical indicators 804, 806, 808, 810, 812, 814, 816, 818, 820, 822, 824, 826, 828, 830, 832, 834, 836, 838, and 840. Areas include areas 842, 844, 846, 848, 850, 852, 854, 856, 858, 860, 862, 864, 866, 868, 870, 872, 874, 876, and 878. Graphical indicators 804-840 are displayed on image 800 on display device 802 in association with areas 842-878, respectively, on image 800. Additionally, timestamp 880 is also displayed on image 800. Timestamp 880 is an indicator of the time at which image 800 was generated.

Areas 841 are the areas on each image in the sequence of images that were analyzed. In other words, in this illustrative example, areas 841 outlined by graphical indicators 803 on image 800 are the areas that were analyzed in the sequence of images to identify changes in these areas between consecutive images sufficient to identify images as images of interest. Consecutive images are images in the sequence of images without any other additional images in between the consecutive images.

For example, graphical indicators 803 indicate the areas that may be compared between a first image in the sequence of images and a second image in the sequence of images. The first image is any image in the sequence of images. The second image is a subsequent image to the first image. In other words, the second image is an image after the first image without any other images in between the two images. In this manner, the first image and the second image are consecutive images.

In this illustrative example, the display of graphical indicators 803 in association with areas 841 on image 800 on display device 802 allows the person viewing display device 802 to identify all the areas that were analyzed for selecting the images of interest to be displayed on display device 802.

Figure 9:
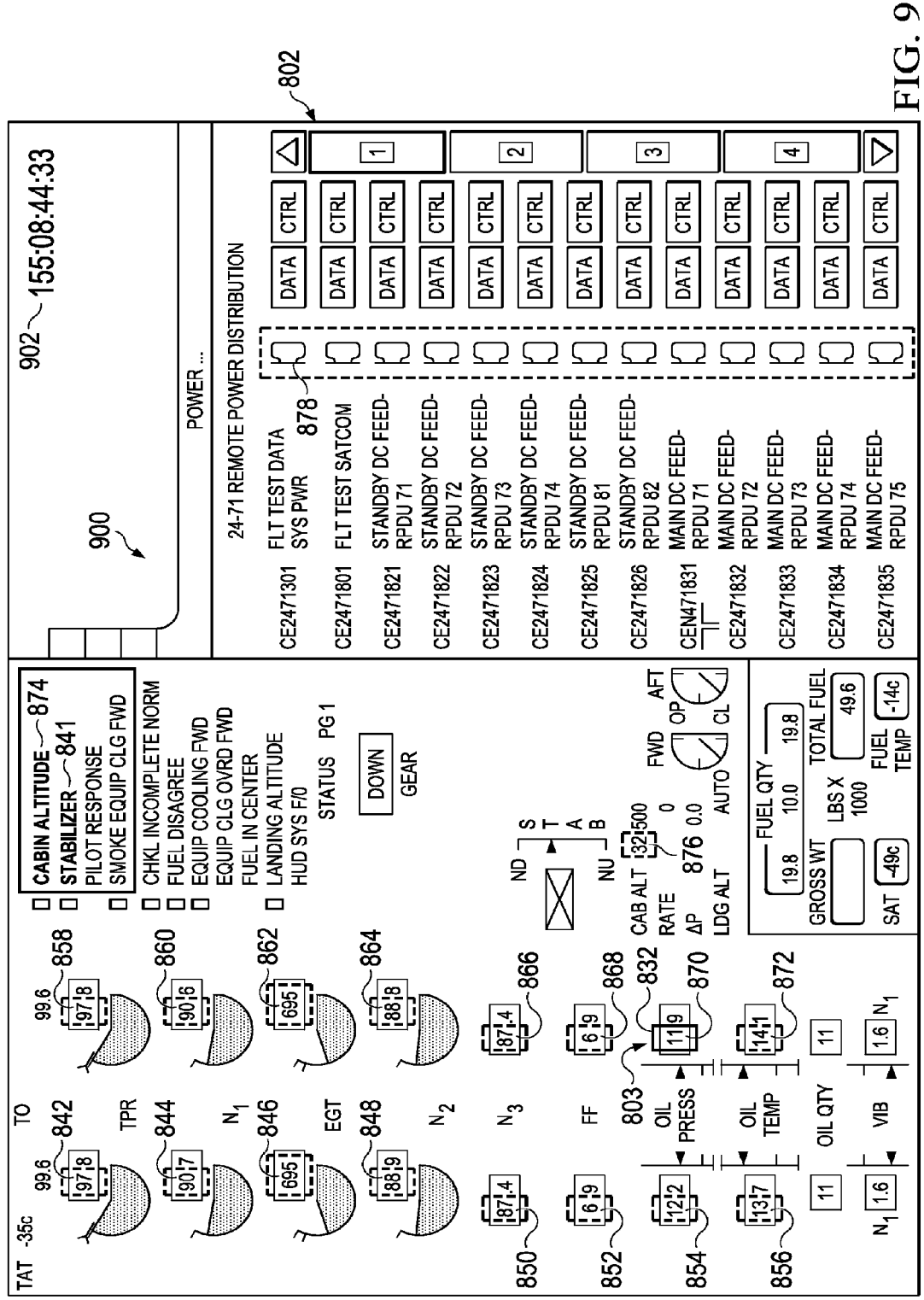
FIG. 9 is an illustration of an image displayed on a display device in accordance with an advantageous embodiment.

With reference now to FIG. 9, an illustration of an image displayed on a display device is depicted in accordance with an advantageous embodiment. In this illustrative example, image 900 is displayed on display device 802 from FIG. 8. Image 900 is an image that is after image 800 in FIG. 8 in the sequence of images captured by the camera system.

Image 900 is selected for display on display device 802 because image 900 is an image of interest. In this illustrative example, image 900 is the first image after image 800 in the sequence of images that had a change in an area in areas 841 sufficient to identify image 900 as an image of interest.

In this illustrative example, graphical indicator 832 from FIG. 8 is displayed on image 900 on display device 802 in association with area 870 on image 900. Area 870 on image 900 is the same area as area 870 on image 800 in FIG. 8. The presence of graphical indicator 832 in association with area 870 on image 900 indicates that a change occurred in area 870 between image 900 and the image preceding image 900 in the sequence of images.

Additionally, as depicted, graphical indicator 832 is the only graphical indicator in graphical indicators 803 from FIG. 8 displayed on image 900. The absence of these other graphical indicators in association with the other areas in area 841, other than area 870 on image 900, indicates that a change was not present in these other areas between image 900 and the image preceding image 900 sufficient to identify image 900 as an image of interest.

Further, image 900 has timestamp 902. Timestamp 902 indicates the time at which image 900 was generated. Timestamp 902 may be used to identify any events occurring at the time that image 900 was generated that may be related to the change identified in area 870. In other words, timestamp 902 may be used to correlate the change in area 870 with one or more events occurring at the time indicated by timestamp 902.

The event may be, for example, without limitation, a test, an operation to change a parameter for a component in the aircraft, a change in the phase of flight for the aircraft, an activation of a component or system in the aircraft, and/or some other suitable event.

Other images of interest in the sequence of images may be displayed to the person at display device 802 in a manner similar to image 900.

Figure 10:
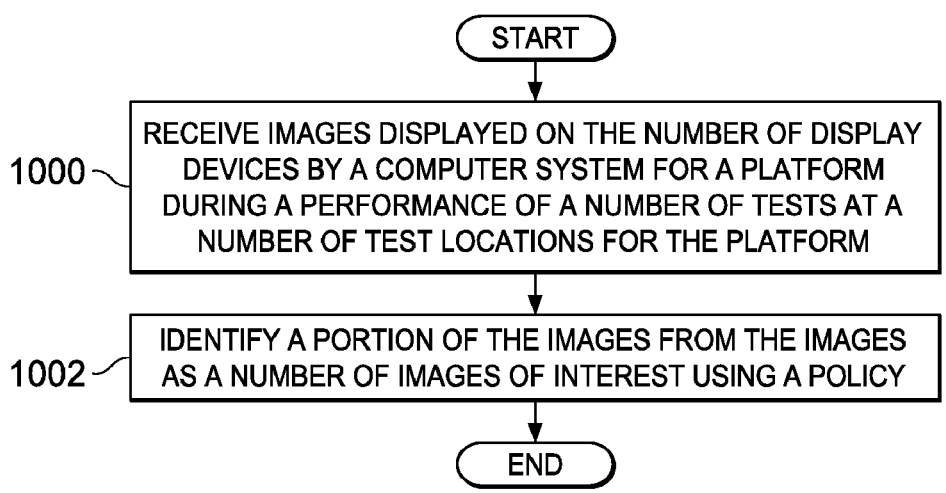
FIG. 10 is an illustration of a flowchart of a process for testing a number of display devices in accordance with an advantageous embodiment.

With reference now to FIG. 10, an illustration of a flowchart of a process for testing a number of display devices is depicted in accordance with an advantageous embodiment. The process illustrated in FIG. 10 may be implemented in platform display testing environment 300 in FIG. 3.

The process begins by receiving images displayed on the number of display devices by a computer system for a platform during a performance of a number of tests at a number of test locations for the platform (operation 1000). The number of display devices and the computer system are located on the platform.

Thereafter, the process identifies a portion of the images from the images as a number of images of interest using a policy (operation 1002), with the process terminating thereafter. The policy may be, for example, policy 348 in FIG. 3. The policy used in operation 1002 may include a number of rules and/or data that indicates or specifies when an image is an image of interest.

Figure 11:
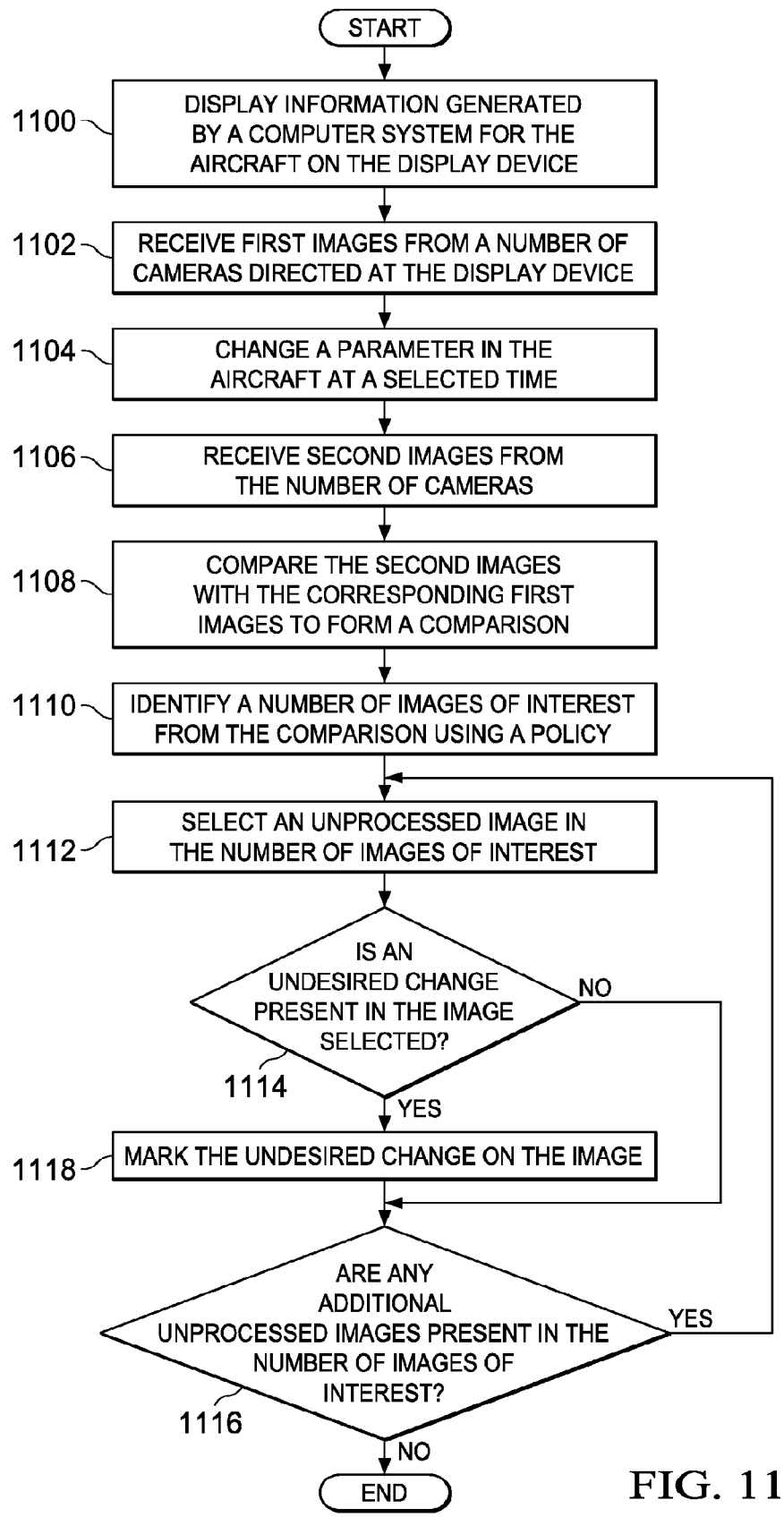
FIG. 11 is an illustration of a flowchart of a process for testing a display device for an aircraft in accordance with an advantageous embodiment.

With reference now to FIG. 11, an illustration of a flowchart of a process for testing a display device for an aircraft is depicted in accordance with an advantageous embodiment. The process illustrated in FIG. 11 may be implemented in platform display testing environment 300 in FIG. 3.

The process begins by displaying information generated by a computer system for the aircraft on the display device (operation 1100). The information may be, for example, an image and/or a number of graphical indicators displayed on the display device. The process then receives first images from a number of cameras directed at the display device (operation 1102). The first images comprise first timestamps for the first images.

Thereafter, the process changes a parameter in the aircraft at a selected time (operation 1104). Changing the parameter may be, for example, at least one of changing a current in a component in the aircraft, introducing radio frequency signals to a component in the aircraft, applying an electrical discharge to the aircraft, or some other suitable type of change.

The selected time may be any time during which a change is desired in the parameter. For example, the selected time may be a point in time at which a test is performed on a component in the aircraft. In another example, the selected time may be selected after the aircraft has been operating for some period of time, during a particular phase of flight, or some other suitable time.

The process then receives second images from the number of cameras (operation 1106). The second images comprise second timestamps for the second images. Next, the process compares the second images with the corresponding first images to form a comparison (operation 1108).

The process identifies a number of images of interest from the comparison using a policy (operation 1110). The policy may be, for example, policy 348 in FIG. 3. Thereafter, the process selects an unprocessed image in the number of images of interest (operation 1112). In some illustrative examples, selection of the unprocessed image may include, for example, displaying the unprocessed image on a display device for a person to view the unprocessed image.

The process then determines whether an undesired change is present in the image selected (operation 1114). Operation 1114 may be performed by a person viewing the image selected and the person using his or her experience and/or a policy to determine whether the undesired change is present.

If an undesired change is not present, the process determines whether any additional unprocessed images are present in the number of images of interest (operation 1116). If additional unprocessed images are not present, the process terminates. Otherwise, the process returns to operation 1112 as described above.

With reference again to operation 1114, if an undesired change is present, the process marks the undesired change on the image (operation 1118). Thereafter, the process proceeds to operation 1116 as described above.

Figure 12:
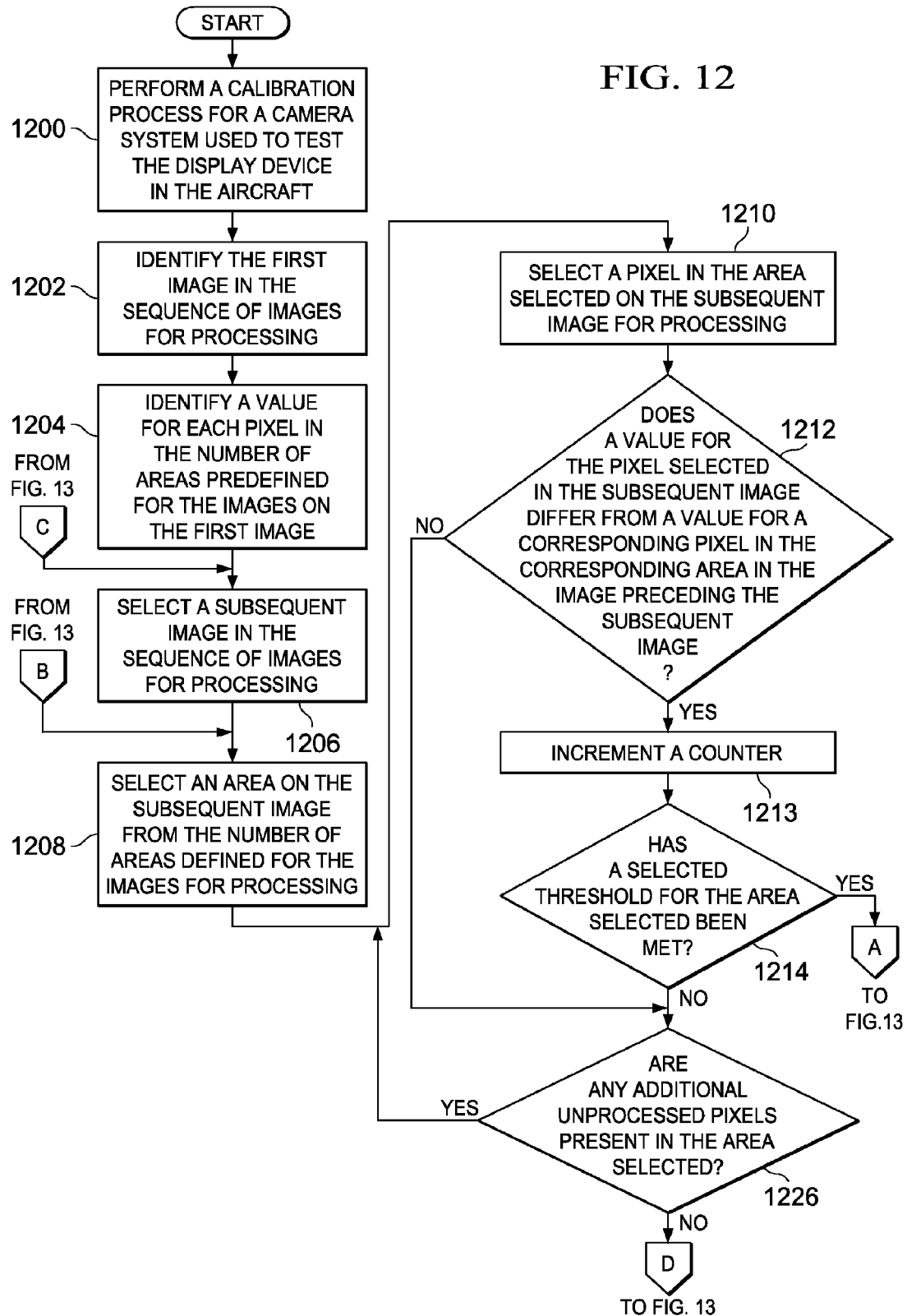
FIGS. 12 and 13 are illustrations of a flowchart of a process testing a display device in an aircraft in accordance with an advantageous embodiment.
Figure 13:
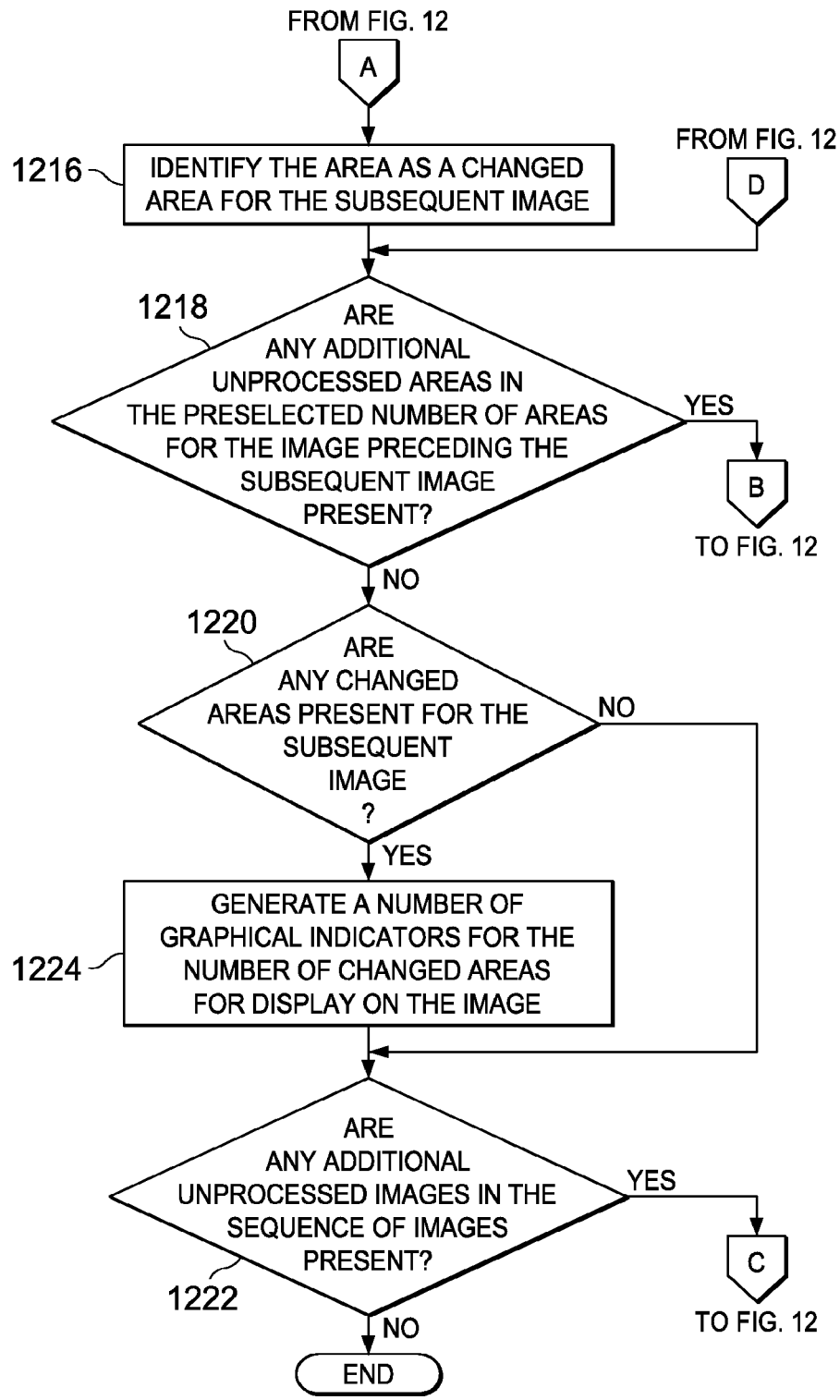

With reference now to FIG. 12 and FIG. 13, illustrations of a flowchart of a process for testing a display device in an aircraft is depicted in accordance with an advantageous embodiment. The process illustrated in FIGS. 12 and 13 may be implemented in platform display testing environment 300 in FIG. 3.

The process begins by performing a calibration process for a camera system used to test the display device in the aircraft (operation 1200). The camera system may be a video camera system configured to generate a video stream of what is displayed on the display device. The video stream comprises a sequence of images that may also be referred to as a sequence of frames.

In operation 1200, the calibration process includes adjusting the camera system such that a number of areas predefined for the images in the video stream generated by the camera system substantially align to a number of areas on the display device to be analyzed. For example, a number of areas on the display device may contain information of interest. As one illustrative example, one area on the display device may include information about a speed of the aircraft. Another area on the display device may include information about an altitude of the aircraft. Additionally, the calibration process may include other steps.

The process then identifies the first image in the sequence of images for processing (operation 1202). Next, the process identifies a value for each pixel in the number of areas predefined for the images on the first image (operation 1204). For example, each pixel may have a value for each of the attributes, such as, for example, red, green, and blue. In this illustrative example, the value for each pixel attribute may range from about zero to about 255.

Thereafter, the process selects a subsequent image in the sequence of images for processing (operation 1206). The subsequent image is the image after the current image without any other images in between the two images in the sequence of images. The first time operation 1206 is performed, the current image is the first image in the sequence of images, and the subsequent image is the image after the first image, which is the second image in the sequence of images.

The process then selects an area on the subsequent image from the number of areas defined for the images for processing (operation 1208). The first time operation 1208 is performed, the image preceding the subsequent image is the first image in the sequence of images, and the preselected number of areas is the number of areas predefined for the images. Next, the process selects a pixel in the area selected on the subsequent image for processing (operation 1210).

A determination is made as to whether a value for the pixel selected in the subsequent image differs from a value for a corresponding pixel in the corresponding area in the image preceding the subsequent image (operation 1212). If the value for the pixel selected in the subsequent image differs from the value for the corresponding pixel in the image preceding the subsequent image, the process increments a counter (operation 1213). The counter is for the number of pixels in the area selected that have a value different from the value for the corresponding pixels in the image preceding the subsequent image.

Thereafter, the process determines whether a selected threshold for the area selected has been met (operation 1214). Operation 1214 is performed using the counter. In operation 1214, the selected threshold is a percentage of pixels from the total number of pixels in the area selected in the subsequent image that is different from the corresponding pixels in the image preceding the subsequent image.

In operation 1214, if the selected threshold for the area selected has been met, the area is identified as a changed area for the subsequent image (operation 1216). A changed area is an area in the number of areas predefined for the images on the subsequent image that is different from the corresponding area in the image preceding the subsequent image.

Next, the process determines whether any additional unprocessed areas in the preselected number of areas for the image preceding the subsequent image are present (operation 1218). If additional unprocessed areas are present, the process returns to operation 1208 as described above. Otherwise, the process determines whether any changed areas are present for the subsequent image (operation 1220). If changed areas are not present for the subsequent image, the process determines whether any additional unprocessed images in the sequence of images are present (operation 1222). If additional unprocessed images are not present, the process terminates. Otherwise, the process returns to operation 1206 as described above.

With reference again to operation 1220, if changed areas are present for the subsequent image, the process generates a number of graphical indicators for the number of changed areas for display on the image (operation 1224). Thereafter, the process proceeds to operation 1222 as described above.

With reference again to operation 1214, if the selected threshold for the area selected has not been met, the process determines whether any additional unprocessed pixels are present in the area selected (operation 1226). If additional unprocessed pixels are present, the process returns to operation 1210 as described above. Otherwise, if unprocessed pixels are not present, the process proceeds to operation 1218 as described above.

With reference again to operation 1212, if the value for the pixel selected in the subsequent image does not differ from the value for the corresponding pixel in the image preceding the subsequent image, the process proceeds to operation 1226 as described above.

In this illustrative example, after the process described in FIGS. 12 and 13 have been performed, the images, along with the number of graphical indicators generated for the different images, may be displayed on a display device to a person, such as an analyst, using a graphical user interface.

Figure 14:
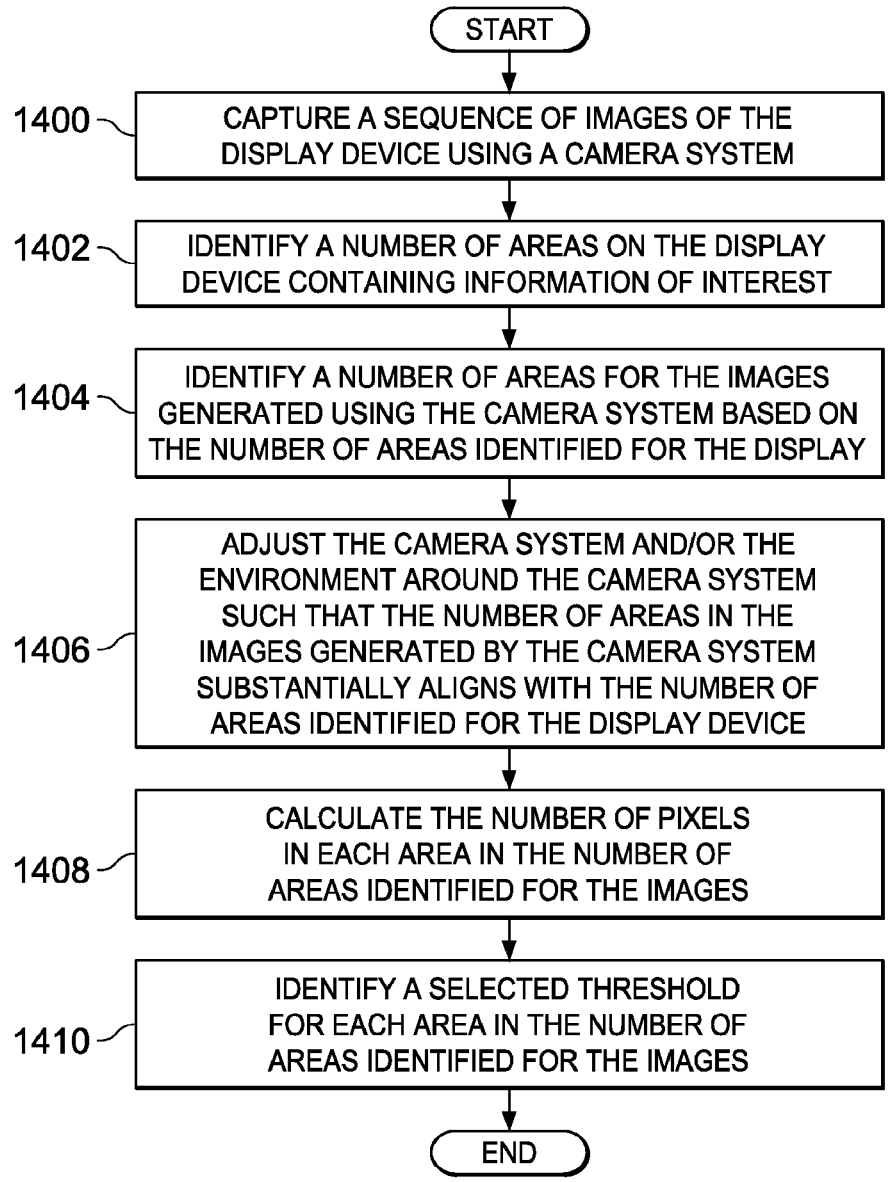
FIG. 14 is an illustration of a flowchart of a process for calibrating a camera system for testing a display device in accordance with an advantageous embodiment.

With reference now to FIG. 14, an illustration of a flowchart of a process for calibrating a camera system for testing a display device in an aircraft is depicted in accordance with an advantageous embodiment. The process illustrated in FIG. 14 may be implemented in platform display testing environment 300 in FIG. 3. Further, this process is a more-detailed process of operation 1200 in FIG. 12.

The process begins by capturing a sequence of images of the display device using a camera system (operation 1400). The camera system is a video camera system used to generate a video stream comprising the sequence of images. The process then identifies a number of areas on the display device containing information of interest (operation 1402). In operation 1402, the number of areas identified on the display device is the number of areas on the display device to be tested.

Thereafter, the process identifies a number of areas for the images generated using the camera system based on the number of areas identified for the display (operation 1404). The process then adjusts the camera system and/or the environment around the camera system such that the number of areas in the images generated by the camera system substantially aligns with the number of areas identified for the display device (operation 1406). In other words, in operation 1406, the camera system is adjusted such that all the information of interest in the number of areas identified on the display device is present within the number of areas identified for the images.

Next, the process calculates the number of pixels in each area in the number of areas identified for the images (operation 1408). Then, the process identifies a selected threshold for each area in the number of areas identified for the images (operation 1410), with the process terminating thereafter. In these examples, the selected threshold for a particular area may be the percentage of pixels in the total number of pixels in the particular area in an image having values that are different from the values for corresponding pixels in another image preceding the image. A percentage of pixels below the selected threshold may be caused by noise or video noise.

The flowcharts and block diagrams in the different depicted embodiments illustrate the architecture, functionality, and operation of some possible implementations of apparatus and methods in different advantageous embodiments. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved. Also, other blocks may be added in addition to the illustrated blocks in a flowchart or block diagram.

Thus, the different advantageous embodiments provide a method and apparatus for testing a number of display devices. Images displayed on the number of display devices by a computer system for a platform are received while a number of tests are performed in a number of test locations for the platform. The process identifies a portion of the images from the images as a number of images of interest using a policy.

The different advantageous embodiments can take the form of an entirely hardware embodiment, an entirely software embodiment, or an embodiment containing both hardware and software elements. Some embodiments are implemented in software, which includes, but is not limited to, forms, such as, for example, firmware, resident software, and microcode.

The description of the different advantageous embodiments has been presented for purposes of illustration and description and is not intended to be exhaustive or limited to the embodiments in the form disclosed. Many modifications and variations will be apparent to those of ordinary skill in the art. Further, different advantageous embodiments may provide different advantages, as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for testing a number of display devices, the method comprising:
receiving images displayed on the number of display devices by a computer system for a platform during a performance of a number of tests at a number of test locations for the platform;
comparing the images to each other to form a comparison, wherein comparing comprises comparing only a number of areas in a first image in the images, the number of areas being less than an entirety of the first image, with a corresponding number of areas in a second image in the images, the corresponding number of areas being less than an entirety of the second image, and wherein the second image is subsequent to the first image;

determining whether any change between the number of areas in the first image and the corresponding number of areas in the second image is sufficient to identify the second image as an image of interest using the policy; and responsive to a determination that the any change is sufficient, identifying the second image as the image of interest using the policy.

2. The method of claim 1, further comprising:
displaying an initial image in the images on a display device; and
displaying a number of graphical indicators on the initial image at the number of areas on the initial image.

3. The method of claim 1, further comprising:
displaying the image of interest on a display device; and
displaying a graphical indicator in association with an area in the number of areas in the image of interest to highlight the any change.

4. The method of claim 1 further comprising:
using changes in the comparison to determine whether the number of display devices perform as desired under different operating conditions for the platform.

5. The method of claim 1 further comprising:
using the number of images of interest to determine whether the display device performs as desired under different operating conditions for the aircraft.

6. The method of claim 1 further comprising:
determining whether an undesired change is present in the image of interest.

7. The method of claim 1, wherein the receiving step comprises:
receiving the images displayed on the number of display devices by the computer system from a camera system directed towards the number of display devices, wherein the images axe received while the number of tests are performed at the number of test locations for the platform.

8. The method of claim 1, wherein the receiving step comprises:
receiving the images displayed on the number of display devices by the computer system from a connection to a graphics adapter generating the images, wherein the images are received while the number of tests are performed at the number of test locations for the platform.

9. The method of claim 1 further comprising:
performing the number of tests at the number of test locations.

10. The method of claim 9, wherein the number of tests comprises at least one of generating radio frequency signals, causing current changes in a system for the platform, generating radio frequency interference, and generating electrical discharges.

11. The method of claim 9, wherein the step of performing the number of tests at the number of test locations comprises:
selecting a component in the platform, wherein the component is at a location in the number of test locations; and
sending test data using the component.

12. The method of claim 1, wherein the platform is selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, and a building.

13. A method for testing a display device for an aircraft, the method comprising:
displaying information generated by a computer system for the aircraft on the display device;
receiving first images from a number of cameras directed at the display device, wherein the first images comprise first timestamps for the first images;
changing a parameter in the aircraft at a selected time;
responsive to a change in the parameter in the aircraft, receiving second images from the number of cameras, wherein the second images comprise second timestamps for the second images;
comparing the second images with corresponding first images to form a comparison, wherein comparing comprises comparing only a number of areas in a first image in the images, the number of areas being less than an entirety of the first image, with a corresponding number of areas in a second image in the images, the corresponding number of areas being less than an entirety of the second image, and wherein the second image is subsequent to the first image; and
determining whether any change between the number of areas in the first image and the corresponding number of areas in the second image is sufficient to identify the second image as an image of interest using the policy; and
responsive to a determination that the any change is sufficient, identifying the second image as the image of interest using the policy.

14. The method of claim 13 further comprising:
determining whether an undesired change is present in the image of interest.

15. An apparatus comprising:
an image acquisition system configured to obtain images generated for display on a number of display devices for a platform during a performance of a number of tests at a number of test locations for the platform; and
a computer system configured to receive the images from the image acquisition system; and identify a portion of the images as a number of images of interest using a policy, wherein the computer system is further configured to display the number of images of interest on a display device and display a number of graphical indicators on the number of images of interest, wherein a graphical indicator displayed on an image of interest in the number of images of interest is associated with an area on the image of interest in which a change between the area on the image of interest and the area on an image in the images preceding the image of interest meets a number of criteria in the policy;
wherein the computer system is further configured to identify the portion of the images by comparing only a number of areas in a first image in the images, the number of areas being less than an entirety of the first image, with a corresponding number of areas in a second image in the images, the corresponding number of areas being less than an entirety of the second image, and wherein the second image is subsequent to the first image;
wherein the computer system is further configured to determine whether any change between the number of areas in the first image and the corresponding number of areas in the second image is sufficient to identify the second image of interest using the policy; and wherein the computer system is further configured to identify, responsive to a determination that the any change is sufficient, the second image as the image of interest using the policy.

16. The apparatus of claim 15, wherein the image acquisition system comprises at least one of a camera system and a media converter.

17. The apparatus of claim 15, wherein the image acquisition system, the computer system, and the display device are associated with the platform.

18. The apparatus of claim 15, wherein the computer system is further configured to determine whether an undesired change is present in the image of interest.

19. An aircraft display system comprising:
a display system associated with an aircraft, wherein the display system comprises a number of display devices;
an image acquisition system associated with the aircraft, wherein the image acquisition system is configured to obtain images generated for display on the display system associated with the aircraft during operation of the aircraft; and
a testing module associated with the aircraft, wherein the testing module is configured to receive the images from the image acquisition system;
wherein the testing module is further configured to identify a portion of the images by comparing only a number of areas in a first image in the images, the number of areas being less than an entirety of the first image, with a corresponding number of areas in a second image in the images, the corresponding number of areas being less than an entirety of the second image, and wherein the second image is subsequent to the first image;
wherein the testing module is further configured to determine whether any change between the number of areas in the first image and the corresponding number of areas in the second image is sufficient to identify the second image as an image of interest using the policy;
wherein the testing module is further configured to identify, responsive to a determination that the any change is sufficient, the second image as the image of interest using the policy; and
wherein the testing module is further configured to display the image of interest on a display device.

20. The aircraft display system of claim 19, wherein the testing module is further configured to determine whether an undesired change is present in the image of interest.

21. The aircraft display system of claim 20, wherein the testing module is further configured to highlight the undesired change in the image of interest on the display device.

* * * * *

UNITED STATES PATENT AND TRADEMARK OFFICE
CERTIFICATE OF CORRECTION

PATENT NO. : 9,448,183 B2  
APPLICATION NO. : 14/275278  
DATED : September 20, 2016  
INVENTOR(S) : Jackson Page 1 of 1

It is certified that error appears in the above-identified patent and that said Letters Patent is hereby corrected as shown below:

In the Claims

Column 25, Line 38, change "axe" to -- are --  
Column 28, Line 12, change "the policy" to -- a policy --

Signed and Sealed this  
Sixth Day of February, 2018

Joseph Matal  
*Performing the Functions and Duties of the*  
*Under Secretary of Commerce for Intellectual Property and*  
*Director of the United States Patent and Trademark Office*